United States Patent
Morrison et al.

(10) Patent No.: US 10,588,638 B2
(45) Date of Patent: Mar. 17, 2020

(54) RADIAL COMPRESSION BAND

(71) Applicant: TZ MEDICAL, INC., Portland, OR (US)

(72) Inventors: Gregory Morrison, Tualatin, OR (US); Michael Morrison, Tualatin, OR (US); John Lubisich, West Linn, OR (US)

(73) Assignee: TZ MEDICAL, INC., Portland, OR (US)

( * ) Notice: Subject to any disclaimer, the term of this patent is extended or adjusted under 35 U.S.C. 154(b) by 314 days.

(21) Appl. No.: 15/255,017

(22) Filed: Sep. 1, 2016

(65) Prior Publication Data
US 2017/0273693 A1 Sep. 28, 2017

Related U.S. Application Data

(60) Provisional application No. 62/313,591, filed on Mar. 25, 2016.

(51) Int. Cl.
*A61B 17/135* (2006.01)
*A61B 17/132* (2006.01)

(52) U.S. Cl.
CPC ........ *A61B 17/135* (2013.01); *A61B 17/1325* (2013.01)

(58) Field of Classification Search
CPC ....... A61B 17/00; A61B 17/12; A61B 17/132; A61B 17/1325; A61B 17/135; A61B 2017/12004; A61F 5/32; A61F 5/34; A61F 5/37; A61F 5/3715; A61F 5/3723; A61H 9/0092
See application file for complete search history.

(56) References Cited

U.S. PATENT DOCUMENTS

| | | |
|---|---|---|
| 4,224,945 A * | 9/1980 | Cohen ................... A61F 5/34 602/53 |
| 6,558,371 B2 | 5/2003 | Dorn |
| 7,498,477 B2 | 3/2009 | Wada et al. |
| D705,428 S | 5/2014 | Cheney et al. |
| D705,429 S | 5/2014 | Cheney et al. |
| 8,759,603 B2 | 6/2014 | Wada et al. |
| 9,107,671 B2 | 8/2015 | Guillot |
| 9,308,000 B2 | 4/2016 | Pancholy |
| 2003/0069528 A1* | 4/2003 | Herz ................... A61H 9/0078 601/152 |
| 2004/0098035 A1* | 5/2004 | Wada ................. A61B 17/1325 606/201 |
| 2013/0310628 A1* | 11/2013 | Chisena ............. A61B 17/1325 600/15 |
| 2014/0142615 A1* | 5/2014 | Corrigan, Jr. ...... A61B 17/1325 606/201 |

(Continued)

FOREIGN PATENT DOCUMENTS

| | | |
|---|---|---|
| JP | 8-71077 A | 3/1996 |
| JP | 2005-218593 A | 8/2005 |

(Continued)

*Primary Examiner* — Robert A Lynch
(74) *Attorney, Agent, or Firm* — patenttm.us

(57) ABSTRACT

A radial compression band employs a substantially rigid U-like cuff that fits over a patient's arm and then snaps onto a tightening band. A movable bubble member is positioned for movement along the band separate from the attachment to the patient and is inflatable to provide pressure to an incision or the like to accomplish hemostasis.

23 Claims, 28 Drawing Sheets

(56) References Cited

U.S. PATENT DOCUMENTS

| | | | | |
|---|---|---|---|---|
| 2015/0018869 A1* | 1/2015 | Benz | ............... | A61B 17/135 |
| | | | | 606/203 |
| 2015/0327870 A1* | 11/2015 | Fortson | ............ | A61B 17/135 |
| | | | | 606/202 |
| 2016/0354091 A1 | 12/2016 | Saatchi et al. | | |

FOREIGN PATENT DOCUMENTS

| JP | 2015-66032 A | 4/2015 |
|---|---|---|
| JP | 2015-066032 A | 4/2015 |
| WO | 2015/060967 A1 | 4/2015 |
| WO | 2015060068 A1 | 4/2015 |
| WO | 2017/039005 A1 | 3/2017 |

\* cited by examiner

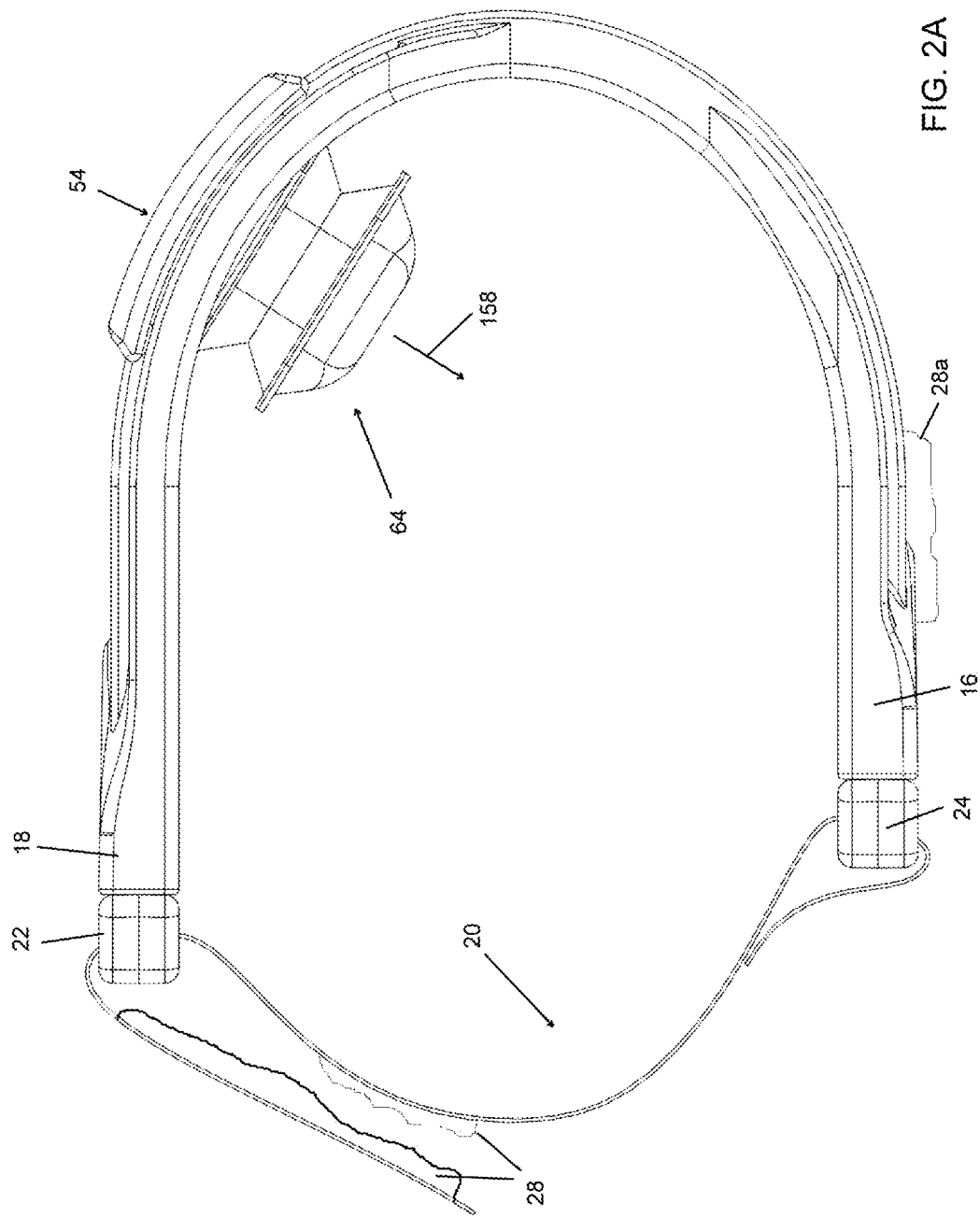

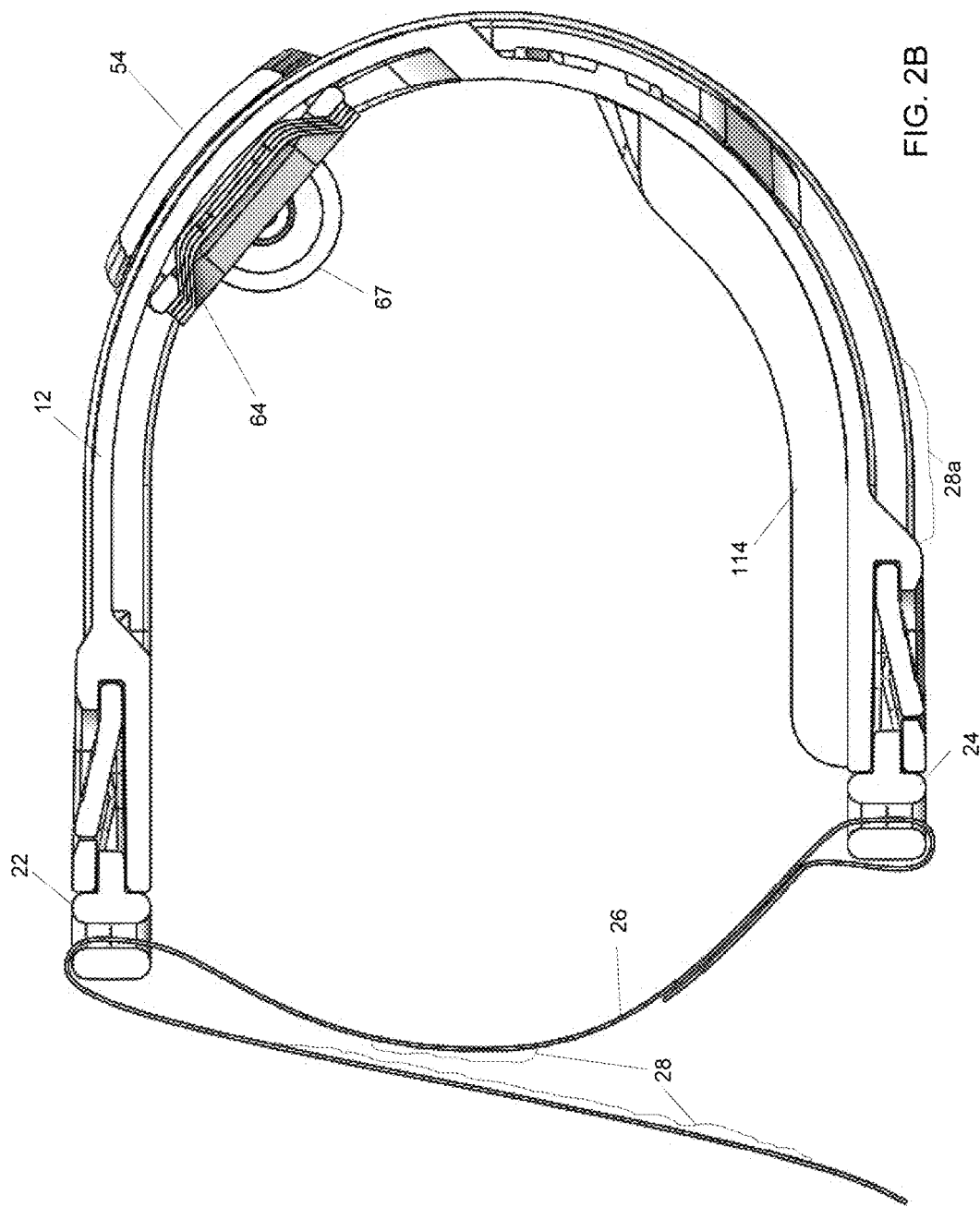

RADIAL COMPRESSION BAND

CROSS-REFERENCE TO RELATED APPLICATIONS

This application claims the benefit of U.S. provisional application filed on Mar. 25, 2016, and having application Ser. No. 62/313,591, the entire contents of which are hereby incorporated herein by reference.

BACKGROUND

This disclosure relates to compression bands, and more particularly to compression bands for use as a hemostatic device on a wrist of a patient.

Radial artery puncture is used to obtain blood samples or otherwise access a patient's artery, for example for obtaining an arterial blood sample for blood gas measurement or for heart catheterization via the radial artery, or other medical procedures. A needle is inserted into the patient's artery to obtain a blood sample. Once the sample is obtained, the needle is removed and pressure is applied to the puncture site for a sufficient period of time to ensure bleeding will not occur, typically for at least 5 minutes. The typical way to apply pressure is to have the phlebotomist press a gauze pad against the puncture site with the phlebotomist's thumb. This requires that the phlebotomist maintain the pressure for sufficient time, which requires the phlebotomist to remain applying consistent pressure during the entire time. It would be desirable to provide a way to apply the pressure in a controlled manner without requiring the phlebotomist to manually press against the puncture site for an extended period of time, freeing the phlebotomist to do other tasks and removing variability in the amount of pressure provided and fatigue or stress to phlebotomist's hand.

Existing solutions to the issues noted above include those described in U.S. Pat. Nos. 7,498,477, 8,481,803, and 8,524,974 all directed to a HEMOSTATIC DEVICE. The devices described in those patents employ a flexible band which wraps around the patient's wrist and is then secured. A syringe is employed to inflate an air bladder which presses against the puncture site.

In use of the device described in the patents, prior to fully removing the needle, catheter or other device that is inserted into the artery, the hemostatic device is put into place on the patient's wrist such that the air bladder is positioned over the puncture site and the patient's wrist is lifted to allow the band to be wrapped around the wrist. Assistance of a 2$^{nd}$ person may in some cases be required at the point of lifting the patient's wrist. The patient's wrist is then lowered again and the band is then secured to close the wrap around the wrist. A syringe filled with air is then attached to the inflation port on the band and air bladder is then inflated to a certain amount, for example, 10 to 18 ml, to apply pressure at the puncture site. The syringe is removed (the air bladder remains inflated by presence of a luer activated valve that maintains air in the bladder in absence of connection of the syringe via the luer lock) and the needle or catheter is then removed. If, as expected, no bleeding is observed, the syringe is re-attached, and a small amount of air is removed from the air bladder, for example, 1 ml. The puncture site is then observed for any bleeding. Air is continued to be removed in approximately 1 ml increments until bleeding is observed, whereupon about 1.5 to 2 ml of air is re-inserted into the bladder to stop the bleeding and achieve non-occlusive hemostatic. The syringe is removed and the band is left in place to allow the puncture site to heal against further bleeding. Every 5 to 15 minutes the syringe may be reattached and a small amount of air removed from the air bladder, to slowly relieve the pressure. A patient might wear the band for several hours in a typical use.

The interface for connection between the air port of the band and the syringe used for inflation and deflation is a tip portion of the syringe that fits into a receptacle attached to a supply tube feeding the air bladder on the band, and is a custom size/shape device, so it becomes important to not lose or damage the original syringe used for inflation when it comes time to deflate the air bladder, as it is then impossible to inflate or deflate the air bladder. If the original syringe is lost or damaged, a new band/syringe package must be opened to obtain a new syringe, leading to extra expense and waste of the unused band that was in the new package.

The use of a flexible band wrapped completely around the patient's arm can lead to tourniquet related issues since the band can be sufficiently tight as to stop or severely reduce blood flow beyond the band.

SUMMARY

In accordance with the disclosure, a substantially rigid partial cuff member is provided to receive the patient's wrist therein, with a securement member to secure the cuff to the wrist. A positionable inflation member is movable along a portion of the cuff to allow positioning of the inflation member over the puncture site without needing to move the cuff. The inflation member is then inflatable to provide pressure against the puncture site, ensure bleeding is prevented.

The subject matter of the present technology is particularly pointed out and distinctly claimed in the concluding portion of this specification. However, both the organization and method of operation, together with further advantages and embodiments thereof, may best be understood by reference to the following description taken in connection with accompanying drawings wherein like reference characters refer to like elements.

BRIEF DESCRIPTION OF THE DRAWINGS

FIG. 2A is a side view of a radial compression band in accordance with the disclosure, with the bubble in an inflated state;

FIG. 2B is a sectional side view of the radial compression band of FIG. 2A, taken along line 2B-2B of FIG. 1, with the bubble in an deflated state;

DETAILED DESCRIPTION

The system according to a preferred embodiment of the present disclosure comprises a substantially rigid partial cuff member, approximately in a U shape, is provided to receive the patient's wrist therein, with a securement strap that is attached to one end of the cuff and adapted to loop through the other end of the cuff, to secure the cuff to the wrist. A positionable inflation member is movable along a portion of the cuff to allow positioning of the inflation member over the puncture site. An inflation port may employ a standard leur lock connector to allow attachment of a syringe for inflation of the inflation member to provide pressure against the puncture site, for achieving non-occlusive hemostatic.

Figure 1:
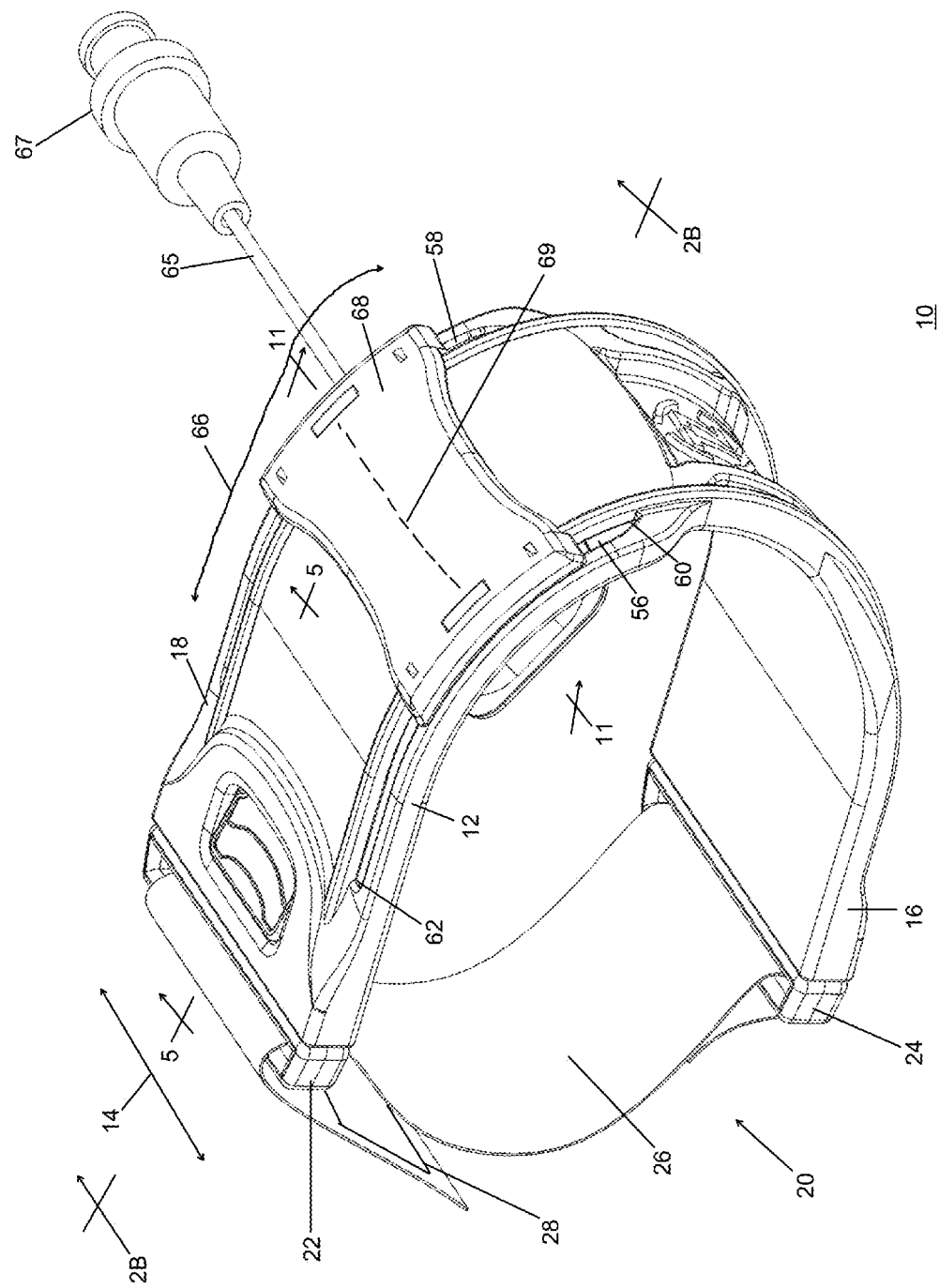
FIG. 1 is a perspective view of a radial compression band in accordance with the disclosure.

Referring to FIG. 1, a perspective view of a radial compression band in accordance with the disclosure, the radial band assembly 10 comprises a radial band brace 12 that is approximately U-shaped and having a width 14, which is adapted to fit over a patient's wrist where the wrist is received in the open central portion of the radial band brace. The band brace is slightly loaded so that the 'legs' of the U-shape are not exactly parallel to one another. In a particular embodiment, the radial band brace can be produced in different sizes, to accommodate different sized patient wrists. Typically a size is chosen that is just slightly larger than the patient's wrist. The band is suitably clear such that it is easily seen through, and may comprise of clear ABS, for example. The band can be provided with a color if desired. Acrylic may be used if rigidity is not an issue. The different sizes can be provided with slight color tints, each size being given a different color, to allow quick identification of which size the band is. The band is substantially rigid, with some amount of flexibility such that when the strap is tightened, the U-shaped legs will move towards each other somewhat to take up slack in the fit on the patient's wrist. Examples of suitable material to use in construction of the band includes PVC, ABS, Poly Urethane, or a blend thereof.

Referring to FIG. 2A, a side view of the radial compression band with the bubble in an inflated state, it may be observed that in the particular embodiment, the U-shaped configuration is a slightly varied U, where one leg 16 of the U portion is shorter than the other, the shorter leg being in the lower portion of FIG. 2, while the upper leg 18 is slightly longer, extending further to the left in the view of FIG. 2.

A strap assembly 20 connects to the ends of the radial band brace, suitably by means of upper and lower buckles 22 and 24, which removably connect to the radial band brace at the 'ends' of the U-shape of the band brace. A strap member 26 is received by the buckles, substantially permanently yet flexibly attached at one of the buckles, lower buckle 24, for example, and removably looped through upper buckle 22. Hook and loop fasteners 28 are provided on the strap member to allow adjustment tightening of the tension on the strap and then securing the strap with the desired tension, allowing the band to be removably secured to the patient's wrist. An optional additional hook and loop material 28a may be provided on the band to secure any excess length of the strap, if desired.

Upper and lower buckles 22 and 24 securely yet detachably engage with the radial band brace, to allow the band to be quickly released from a patient's wrist by disconnection of the engagement. Details of the engagement structure are illustrated in FIGS. 3-5.

Figure 3:
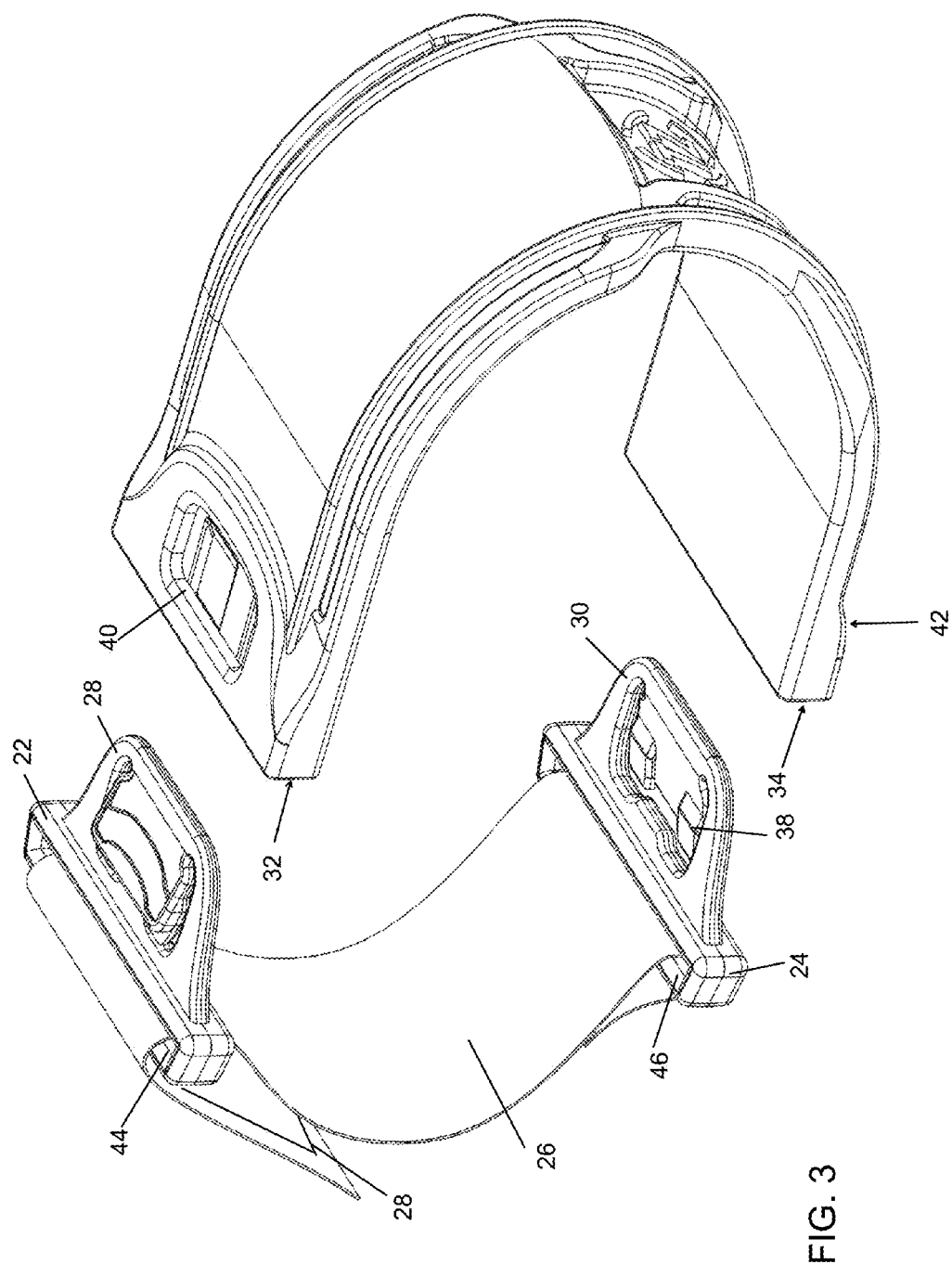
FIG. 3 is a perspective view of a partial radial band to illustrate the connection of the buckles.

Referring to FIG. 3, a perspective view of a partial radial band, the connection of the buckles will be explained. Buckles 22 and 24 have extending tab portions 28, 30 which are sized to be received in corresponding slot portions 32, 34 in the band brace (visible in FIGS. 16 and 17). Considering upper buckle 22, the tab 28 has a curved forward profile defining approximately an isosceles trapezoidal shape and has an upwardly projecting latch portion 36 defined in the center region of the trapezoid. The latch portion 36 is biased to extend above the general plane of the tab in absence of downward force, but is sufficiently flexible to deform if pressed, and returns to the extended position when any such force is removed. Slots 44, 46 provided in the buckles receive the strap 26 therethrough, buckle 22 having the strap pass through in removable fashion, while buckle 24 has the strap looped through then the end of the strap is secured to a portion of the strap to permanently mount the buckle to the strap while still allowing some degree of movement for flexibility. The trapezoidal shape of the buckle extending tab portions provides a narrower width at the end of the tab distal from the attachment to the strap.

Figure 4:
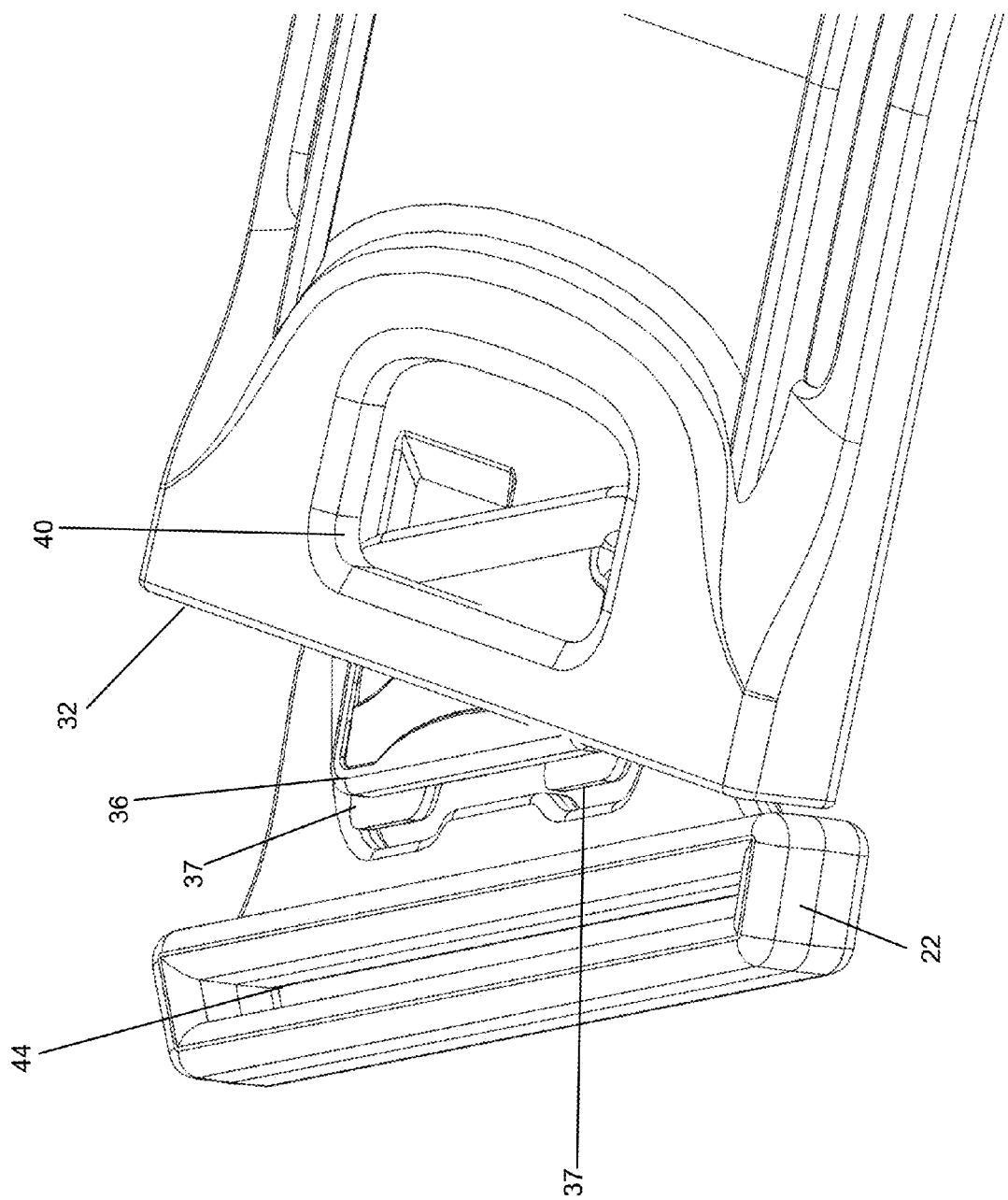
FIG. 4 is a view of a buckle being inserted into the radial band brace.
Figure 5:
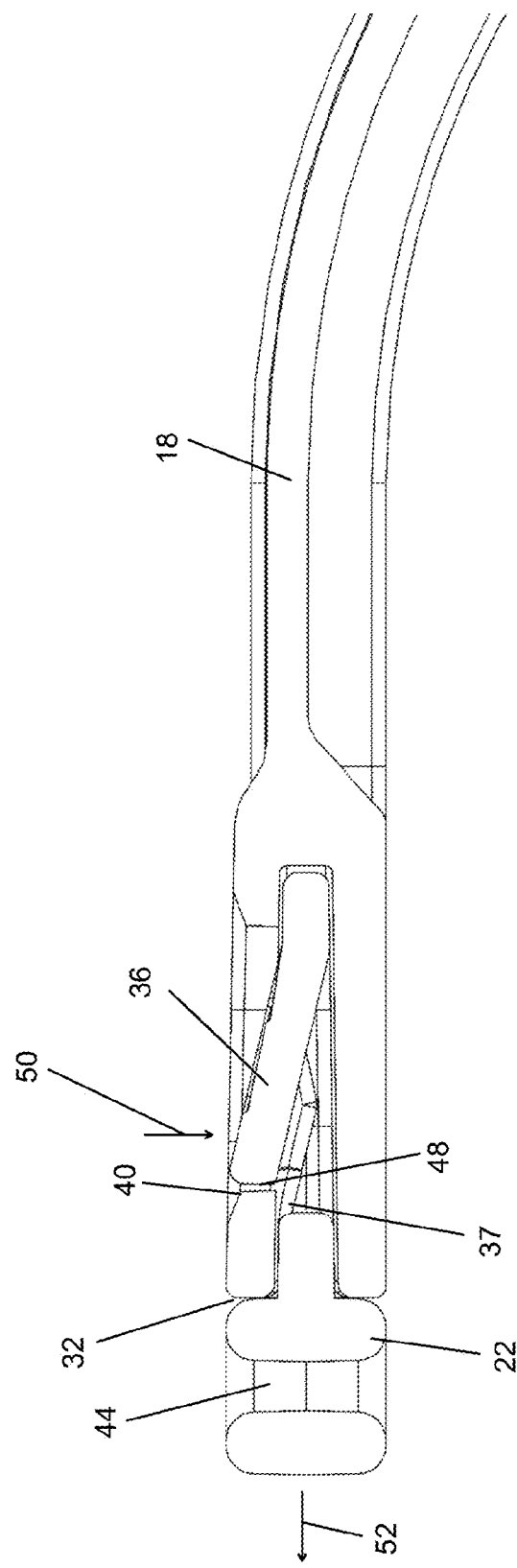
FIG. 5 is a sectional view of the connection portion the buckle taken along line 5-5 of FIG. 1.

With reference to FIG. 4, a view of a buckle being inserted into the radial band brace, the curved narrower end of the trapezoidal shape allows easy insertion of the tab into the receiving slots 32, 34, allowing insertion from the side, without requiring that the tab be square to the opening. The receiving slots provide for the tab portions to be inserted to the slots, which upon insertion, the interaction of the raised latch portion with the receiving slots, which have a height less than the height of the raised latch portion, compresses the latch portion 36. As the tab is further guided into the slot, eventually the latch portion will align with opening 40 defined in the band (opening 42 on the other end of the band) which relieves the compressing force on the latch, allowing the latch to return to its extended position and, operating to lock the buckle to the radial band brace 12. Removal of the device can be quickly accomplished by depressing the latch member 36 (38) which allows the buckle to be withdrawn from the slot, freeing the device from the patient's wrist.

The latch portion 36 has an additional forwardly extending tab portion 37 (two such tabs being provided in the illustrated embodiment) that interacts with the lower face of the upper leg 18 around the opening 40, preventing the latch portion from riding up out of the opening via the top of the opening, which could prevent the removal of the latch when pulling on the strap when trying to remove buckle 22.

Referring to FIG. 5, a sectional view of the connection portion the buckle taken along line 5-5 of FIG. 1 (with the strap removed), the interaction of the latch 36 with the opening 40 can be observed when the tab is fully inserted into the slot 32. Latch 36 is fully extended upwardly, whereby the face 48 of the latch will interact with the edge of the opening 40 to prevent removal of the buckle. Upon depressing the latch in the direction of arrow 50, the face of the latch is lowered to align with the opening of the slot 32, allowing the buckle to be pulled out of the slot in the direction of arrow 52. The interaction of tab portion 37 with the bottom of the radial band brace at the opening 40 may also be observed in FIG. 5, where the upper face of the tab seats against the lower face of the band brace adjacent of the opening 40. By this, the latch portion does not ride up over the walls of the opening 40, which could jam the latch against removal.

Referring again to FIG. 1 and FIG. 2A, the device includes a radial band bubble assembly, which is slidingly movable along an extent of the band, the extent of movement allowed, illustrated by arrow 66, being defined by slots 56, 58 which extend from the top to the underside portion of the band from positions 60 to 62 in the illustrated embodiment. The bubble assembly may be moved to a desired position along the extent provided by the slots. On the inner side of the band, the bubble assembly comprises an inflatable bubble 64, which is in pneumatic communication via tube 65 with a connector 67 that allows an inflation source to be connected to inflate or deflate the bubble. Connector 67 suitably comprises a luer lock. A valve (not shown) may be provided to allow inflation/deflation of the bubble as desired, while maintaining the state of inflation of the bubble in absence of inflation pressure or deflation suction. In use, inflation/deflation is provided by attachment of a syringe to the connector 67 to allow a desired amount of inflation of the bubble 64. The insertion of the syringe operates the valve to allow inflation or deflation of the bubble. Removing the syringe causes the valve to close, maintaining the desired pressure. Pressure is applied by the inflated bubble in the direction of arrow 158.

Figure 6:
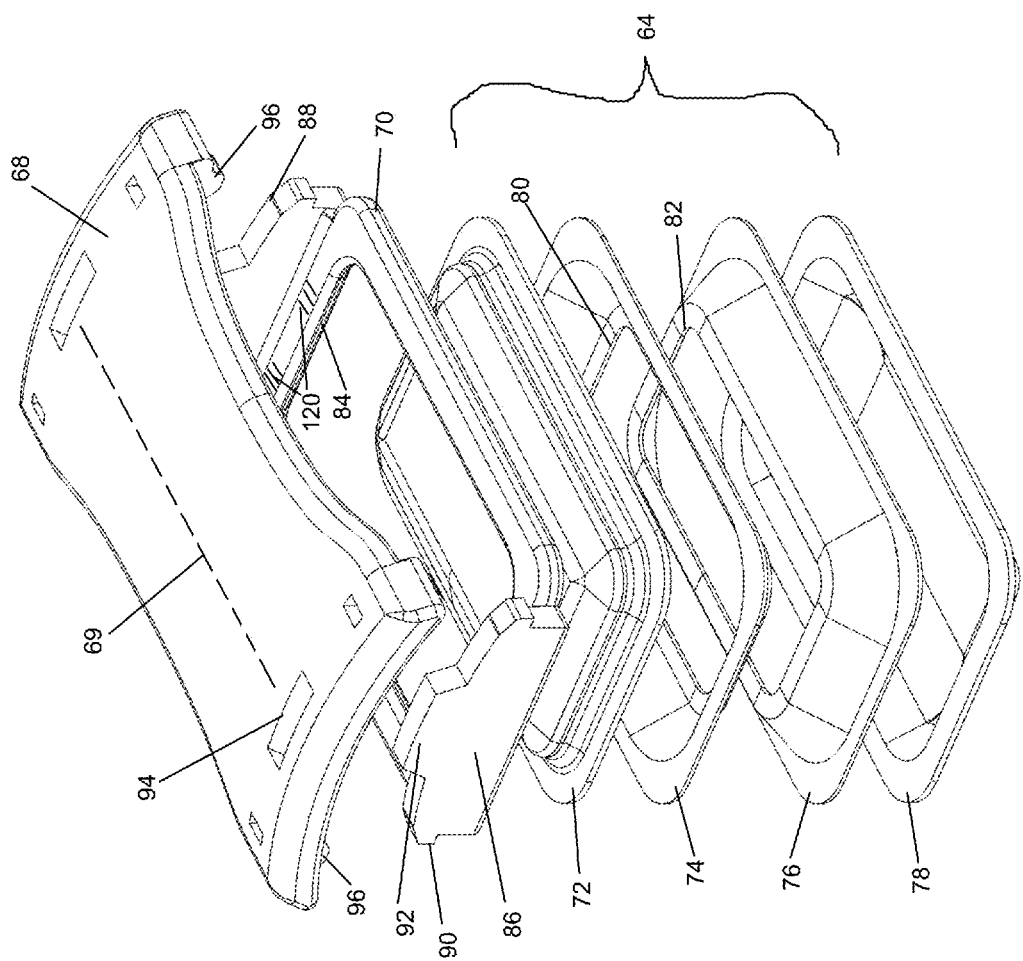
FIG. 6 is an exploded view of the radial band bubble assembly with the bubble in an inflated configuration.
Figure 7:
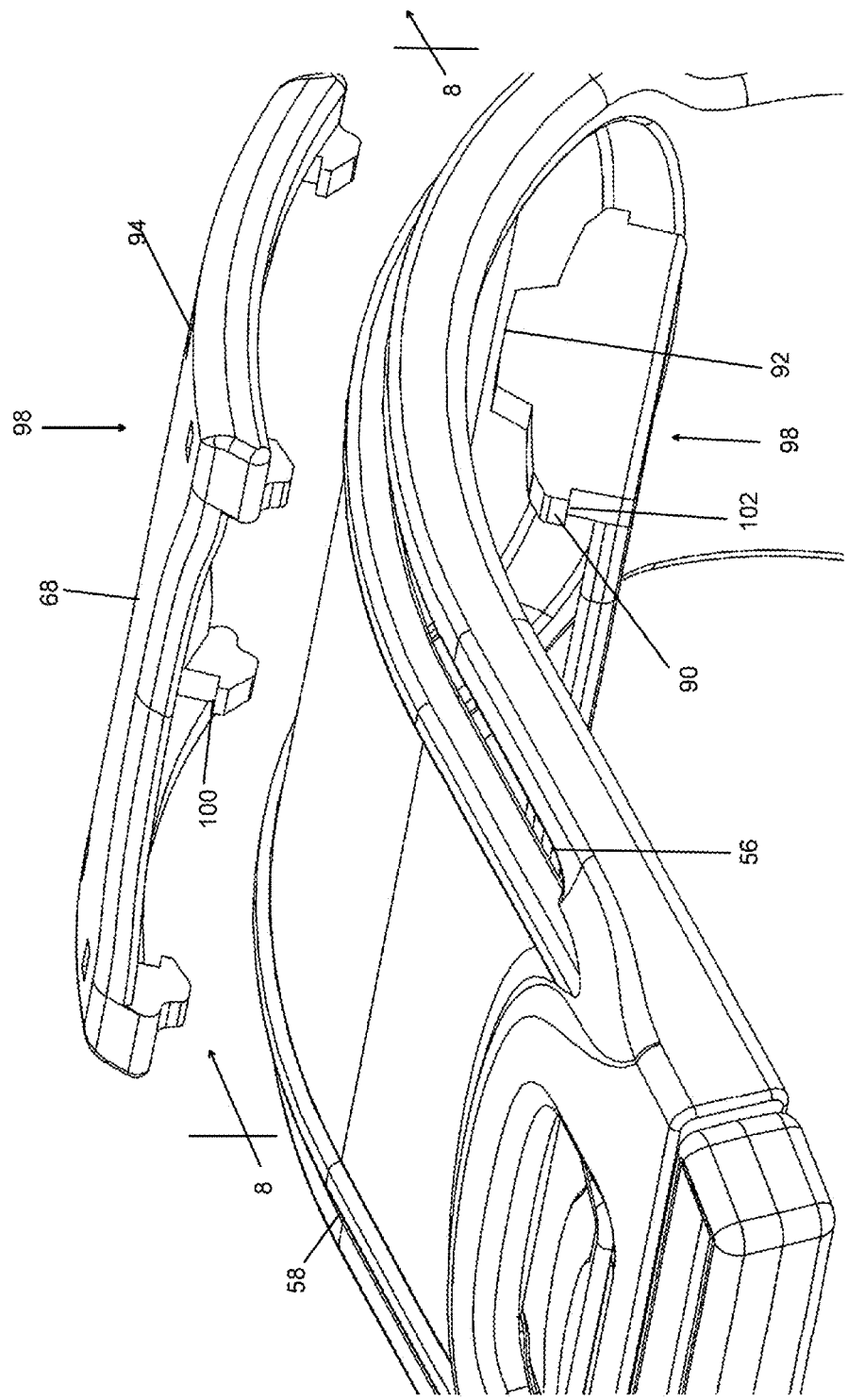
FIG. 7 is a partial perspective view of the radial compression band, without the bubble.
Figure 8:
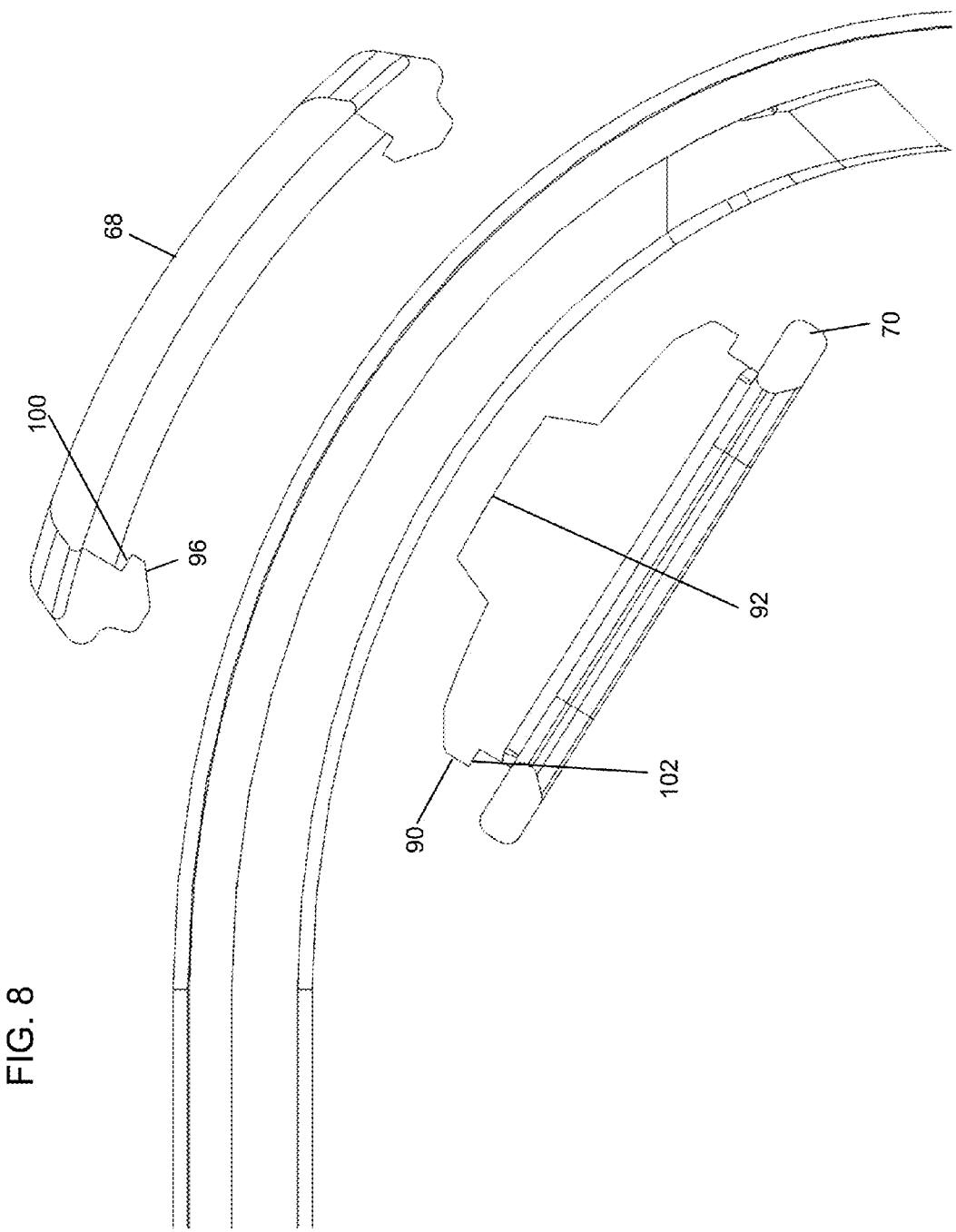
FIG. 8 is sectional view taken along line 8-8 of FIG. 7.

Now referring to FIG. 6, an exploded view of the radial band bubble assembly 54, which comprises, in top to bottom vertical order, a top bubble brace 68, a bottom bubble brace 70 and an accordion bubble having top layer 72, middle layers 74, 76 and bottom layer 78. The middle layers have open center portions 80, 82 to allow passage of air when inflating. Top and bottom layers 72, 78 define closed top and bottom seals for the bubble. Bottom bubble brace 70 has a central opening 84 defined in its substantially rectangular profile, and has upwardly extending end members 86, 88 with outwardly extending tab members 90 defined part way up the vertical height of the end members. A central upwardly projecting tab 92 is defined in the end members. Top bubble brace 68 has corresponding slots 94 which receive tabs 92 therein and tab members 96 oriented downwardly on the lower face of the brace, whereby tabs 92 fit into slots 94 and tabs 90 and 96 snap together to secure the top and bottom bubble braces when the device is assembled. Once so assembled, it is intended that the snap together parts remain permanently secured together. The opening 84 provides a viewing window, and has on the patient facing side a slight recess 85 (visible in FIGS. 10 and 11) so that a patient's skin is not pinched when sliding the bubble assembly. The bottom portion 78 of the bubble provides a smooth contact surface with the patient's skin, without any seam lines or ridges, so no irritation or marking of the skin occurs as could happen if a ridge line were present. In the view of FIG. 6, the bubble portions are in positions when the bubble is inflated FIG. 7 is a partial perspective view of the radial compression band, taken together with FIG. 8, a sectional view along line 8-8 of FIG. 7, to further illustrate the interaction and engagement of the top and bottom bubble braces 68 and 70, with the bubble removed for clarity of illustration. Tab 90 on the bottom brace has an angled surface and tab 96 on the top brace has a similar angled surface, such that when the two brace parts are pushed towards each other in the direction of arrows 98, the two angled surfaces will ride on one another, tabs 96 will move outwardly as a result of flexing of the top brace, allowing the upwardly oriented surface 100 of the top brace to mate with the downwardly oriented surface 102 of the bottom brace, effectively securing the two brace portions together. Upwardly extending end members 86, 88 extend up through slots 56, 58 and tabs 96 extend down through the slots so that the assembled bubble brace can slide along the extent of slots 56 and 58 to allow desired positioning of the bubble when the band is in use. The configuration of the upwardly extending end members 86, 88 and the slots is such that the interaction with the slots prevents biding of the bubble brace if movement pressure is applied at an angle, for example. This is accomplished by the sufficiently long rail-like configuration of the upwardly extending end members, but can also be accomplished by having a 4 pin system with 2 spaced pins on each side interacting with slots 56 and 58.

Figure 9:
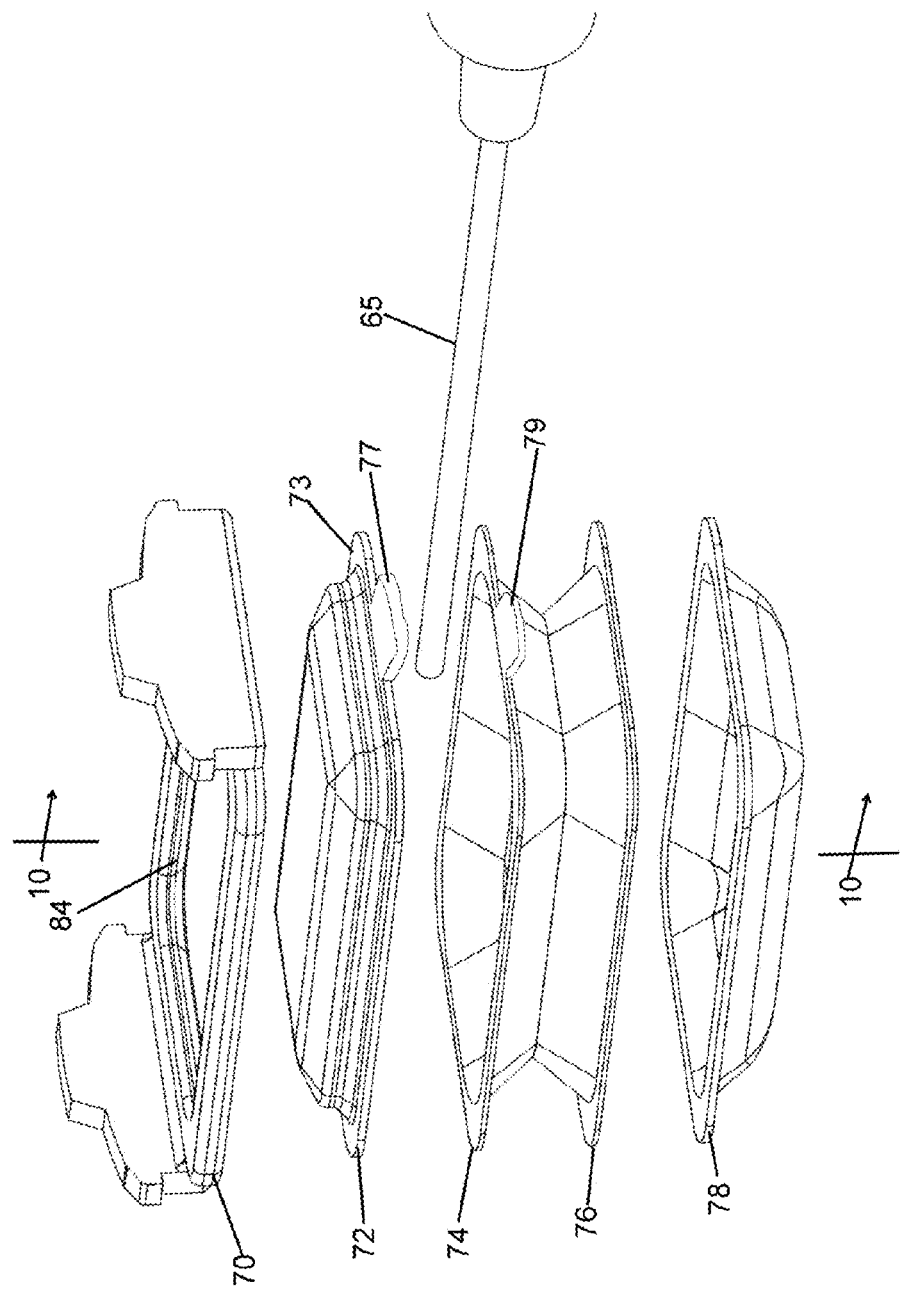
FIG. 9 is an exploded view of a partially constructed bubble assembly.
Figure 10:
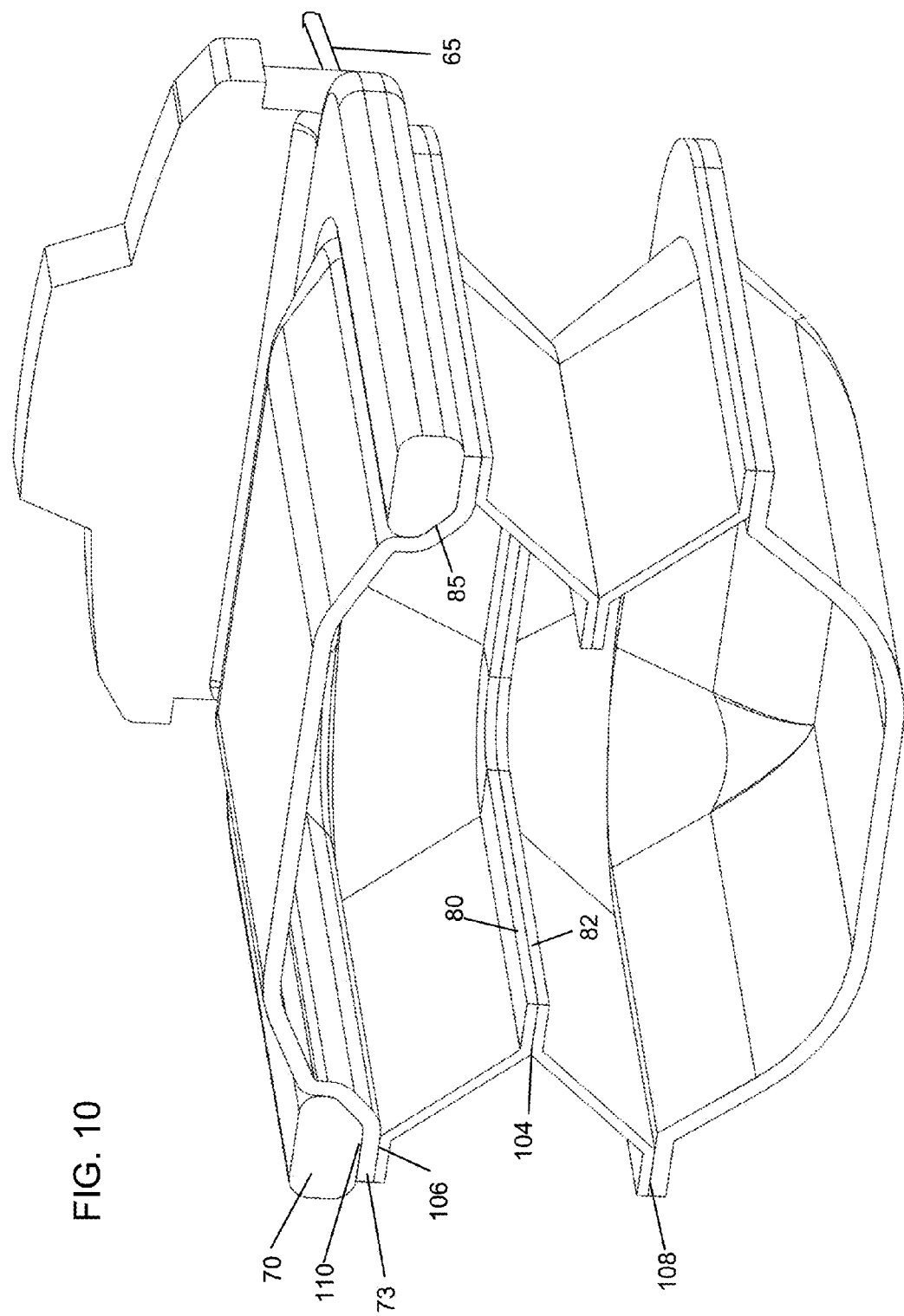
FIG. 10 is a sectional view of a fully constructed bubble assembly taken along line 10-10 of FIG. 9.

Referring to FIG. 9, an exploded view of a partially constructed bubble assembly, and FIG. 10, a sectional view of a fully constructed bubble assembly taken along line 10-10 of FIG. 9, when manufacturing the device, the bubble components 70, 72, 74, 76 and 78 are secured together, by RF welding. First middle layers 74 and 76 are secured to one at joint 104 another along the extents of openings 80, 82. Tube 65 is suitably inserted between layers 72 and 74 and the peripheries of those two layers are secured at joint 106. An extra tab portion 77, 79 can be provided at the edge of layers 72 and 74, to provide additional surface for securing the tube 65 at the point of entry into the bubble. The periphery of bottom layer 78 is secured to the periphery of layer 76 at joint 108, providing an assembled bubble with inflation tube. The dome like upper portion of the top bubble layer 72 is moved into the opening 84 in bottom bubble brace 70 and the bubble is secured thereto at joint 110 along periphery 73. The size of opening 84 is such that the top dome portion of the bubble fits therein.

Figure 26:
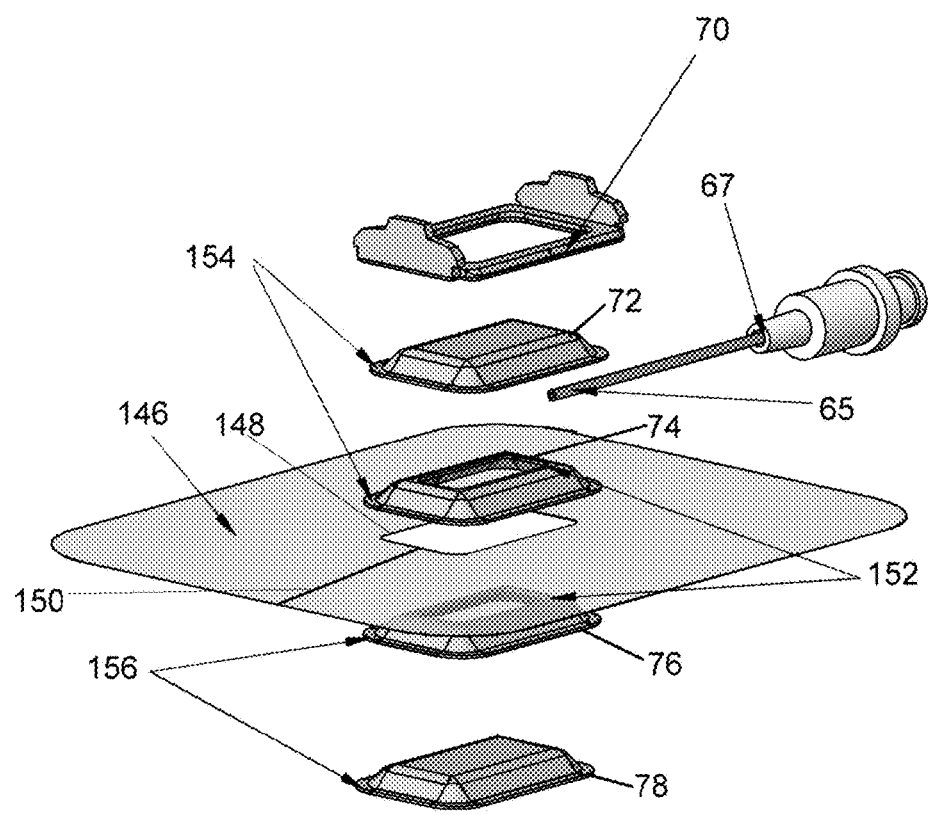
FIG. 26 is an exploded view that illustrates the process of constructing the bubble in manufacturing.

The process of manufacturing the bubble may be understood with reference to FIG. 26, an exploded view of the bubble in the assembly process. The bubble layers are provided in sheets of material, with the bubble shape previously thermoformed in the sheets. In the preferred embodiment, each bubble section is formed to have the same concave shape. Layers 74 and 76 are stacked on each other with the bubbles aligned so as to nest together, and a polytetrafluoroethylene (PTFE) sheet 146, such as a Teflon brand sheet, having an opening 148 is positioned between the two layers 74 and 76. Thermal welding in the shape of the bubble peripheral outline desired is then performed. Joint 104 is thus formed between layers 74 and 76 and the openings 80, 82 are then formed by die cutting the openings in the welded together layers 74, 76. Next, layer 72 is positioned on top of layer 74, by nesting the bubble shape formation of layer 74 on top of the concave bubble wall of layer 74 and the tube 65 which is connected to luer lock 67, is positioned between layers 72 and 74 so that the end of the tube will be contained within the interior of the bubble space once formed, and the periphery of layers 72 and 74 is welded in the outline of the peripheral shape of the bubble, weld 154, to form joint 106, also securing the tube to the bubble. Layer 78 is positioned below layer 76 by nesting the bubble shape of layer 78 with the bubble shape of layer 76 and joint 108 between layer 76 and 78 may be formed, weld 156, again in the peripheral shape of the ultimate bubble shape desired. The polytetrafluoroethylene (PTFE) sheet 146 is employed to properly accomplish the welding, prevents the peripheries of layers 74 and 76 from being welded together in the process, which would prevent the bubble from properly inflating in use. The PTFE sheet has a slit 150 formed from the hole to the outer edge of the PTFE sheet, so that once the bubbles are fully formed, the PTFE sheet may then be pulled out, the slit allowing the sheet to be removed from around the bubble. While a PTFE sheet is shown in the particular embodiment, other materials can be used for the sheet, such as metal, or any other material that will protect against the unintended welding of the peripheries of layers 74 and 76. While illustrated as discrete units shaped as the final bubble in the drawings, the bubble layers are typically provided in the manufacturing process pre-formed in sheets of material, and once welded together, the periphery of the bubble is then die cut out of the stack of the 4 layers of sheets to provide a bubble of the desired dimensions. While a single bubble is shown in FIG. 26 for illustration, in production, multiple bubbles may be formed at a time, such as 4 or more bubbles formed spaced apart in a sheet of material, with a corresponding configuration of PTFE sheet having separate openings 148 corresponding to the configuration of the separate bubbles. The PTFE holes 148 where the bubbles are have corresponding slits 150 from the holes to the outer edge of the PTFE sheet. This way the bubbles are fully formed while still in the sheet form, the PTFE is then pulled away, then the multiple bubbles are die cut out of the stack of the 4 layers all at once or in some sequence of cutting operations. Once die cut to a separate bubble, the bubble may then be adhered to bottom bubble brace 70, either by welding or use of adhesive. The bubble layers are nested together so that the uninflated bubble will assume a resting shape with the layers retracted as in FIG. 18, to be substantially pulled away from a patient's skin when deflated. Suitable material to use in forming the bubble includes PVC or Poly Urethane.

Since the tube 65 inserts above the lower bubble face, when inflated, the tube is lifted above the surface of the patient's skin. Alternatively, the tube can pass through the top bubble brace 68, or through slots 56 or 58

Figure 11:
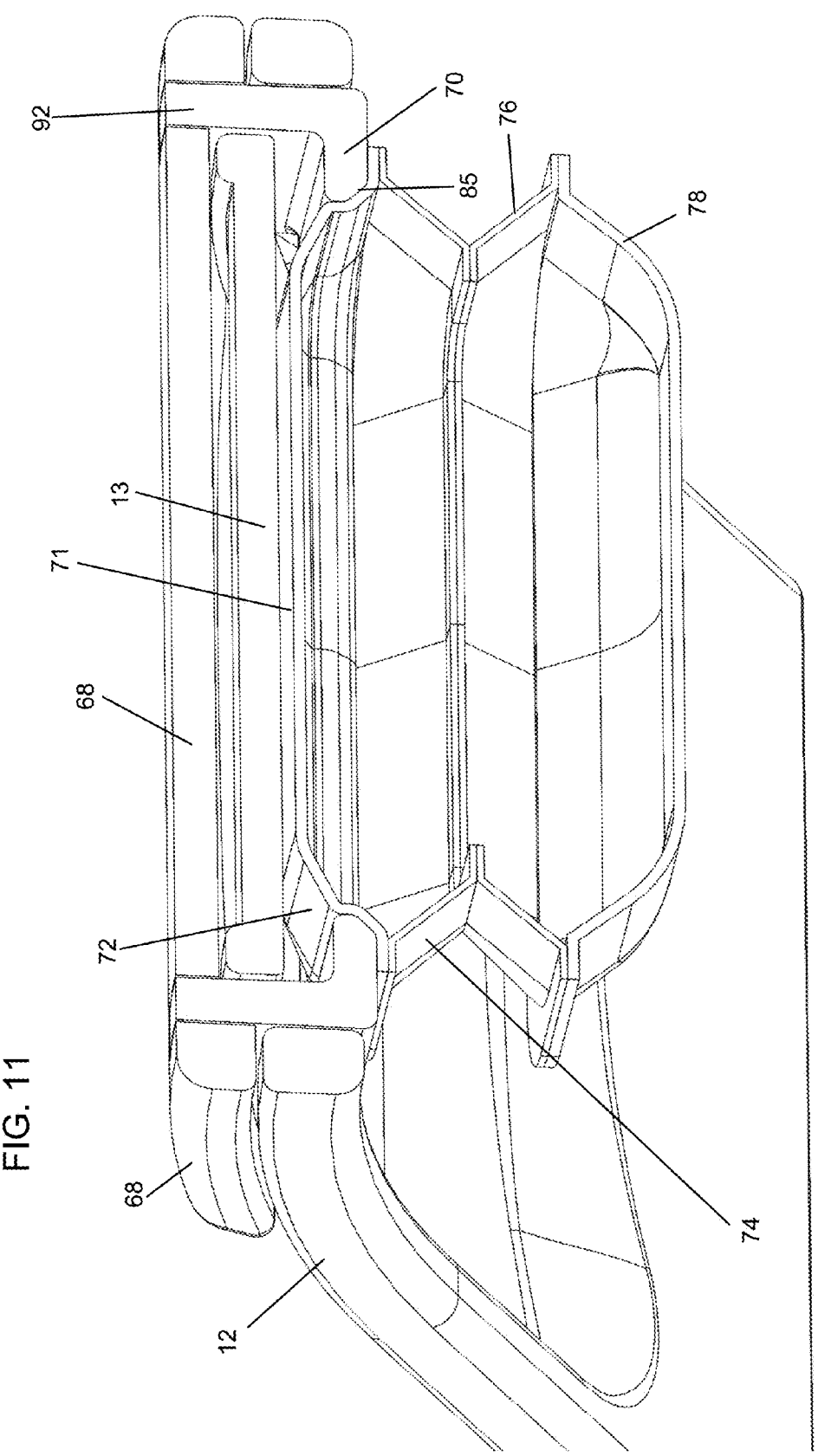
FIG. 11 is a sectional view taken along line 11-11 of FIG. 1.
Figure 18:
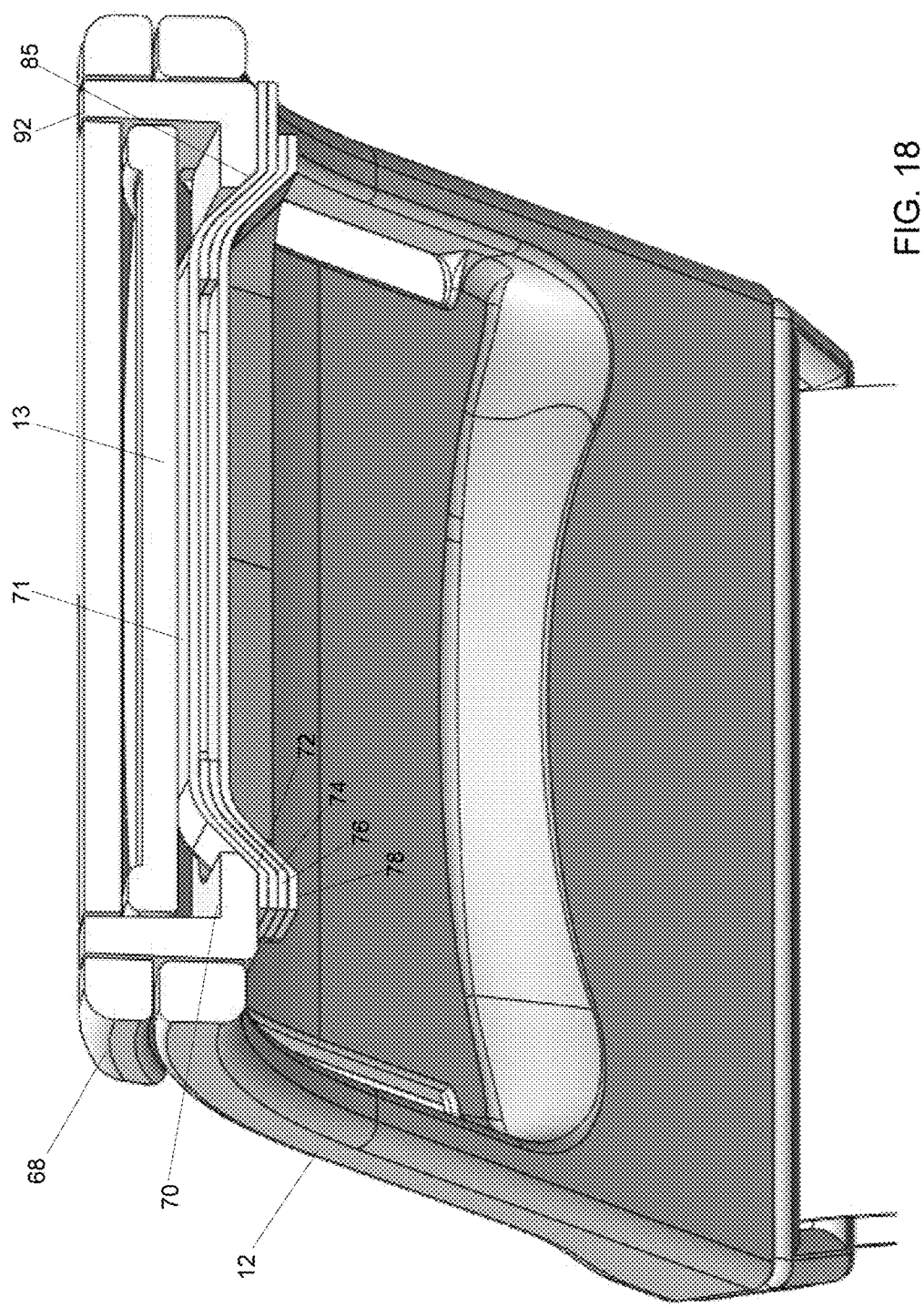
FIG. 18 is a partial perspective sectional view taken along line 11-11 of FIG. 1, but illustrating the bubble in a fully deflated state.

FIG. 11 is a sectional view taken along line 11-11 of FIG. 1, illustrating the fully assembled bubble assembly mounted to the band brace, with the bubble in a fully inflated configuration. Referring to FIG. 18, the configuration of the bubble when deflated can be observed, wherein the various layers of the bubble nest together to allow the bubble to retract within itself, so that the surface of the skin side layer 78 of the bubble is pulled away from the patient's skin and the clot. Also, this configuration assures that no sharp edges are pressing against the patient.

Figure 12:
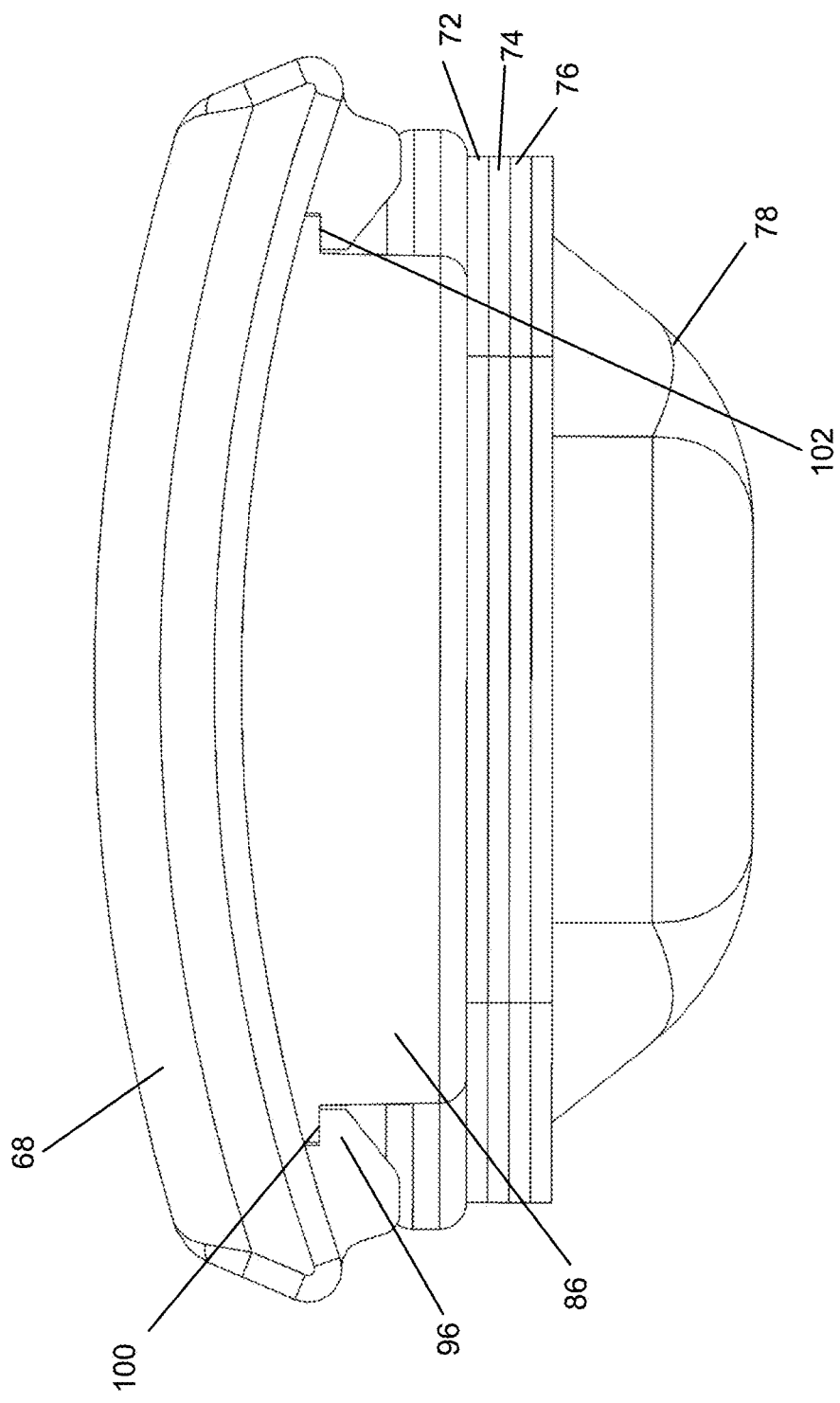
FIG. 12 is a view of the radial band bubble assembly by itself in a partially inflated mode.
Figure 13:
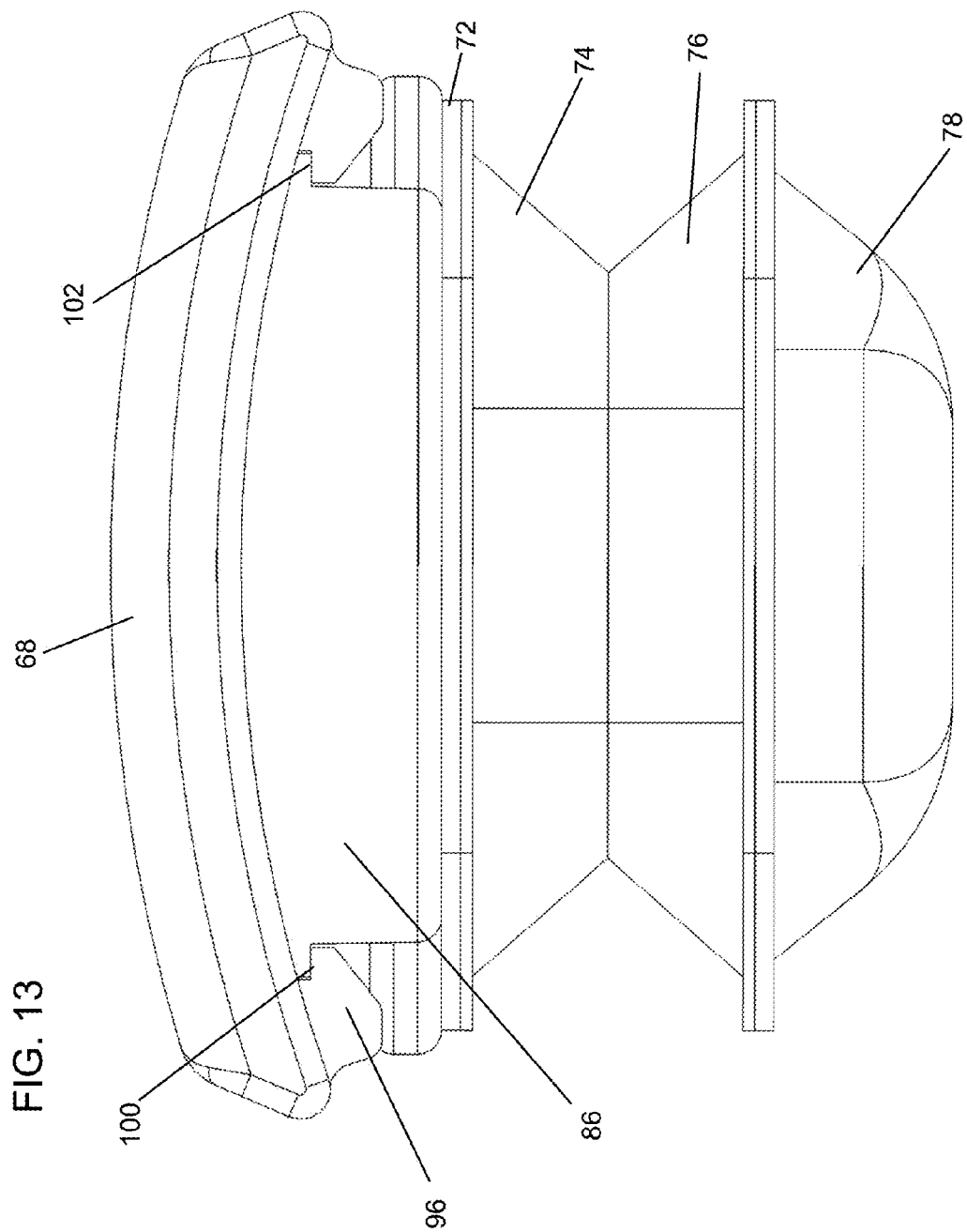
FIG. 13 is a view of the radial band bubble assembly in a fully inflated mode.

FIGS. 12 and 13 show the bubble (with the band removed for illustration purposes) in a partially inflated mode (FIG. 12) where bubble layer 78 has expanded, but substantially the other layers have not yet expanded outwardly, and a fully inflated mode (FIG. 13). FIG. 18 is a partial perspective sectional view illustrating the bubble in a fully deflated state, wherein the bubble is fully collapsed upward into the opening 84 defined in the bottom bubble brace 70. In this fully deflated mode, the central portion of the bubble is pulled away from the patient's body by the collapsing into the opening 84. The various layers 72, 74, 76 and 78 of the bubble sit together in a nested fashion so as to pull away to greatest extent possible from contact with the patient when deflated.

FIG. 2B, a sectional side view of the radial compression band of FIG. 2A, taken along line 2B-2B of FIG. 1, with the bubble in an deflated state, further illustrates the retraction of the bubble into the opening 84.

Figure 14:
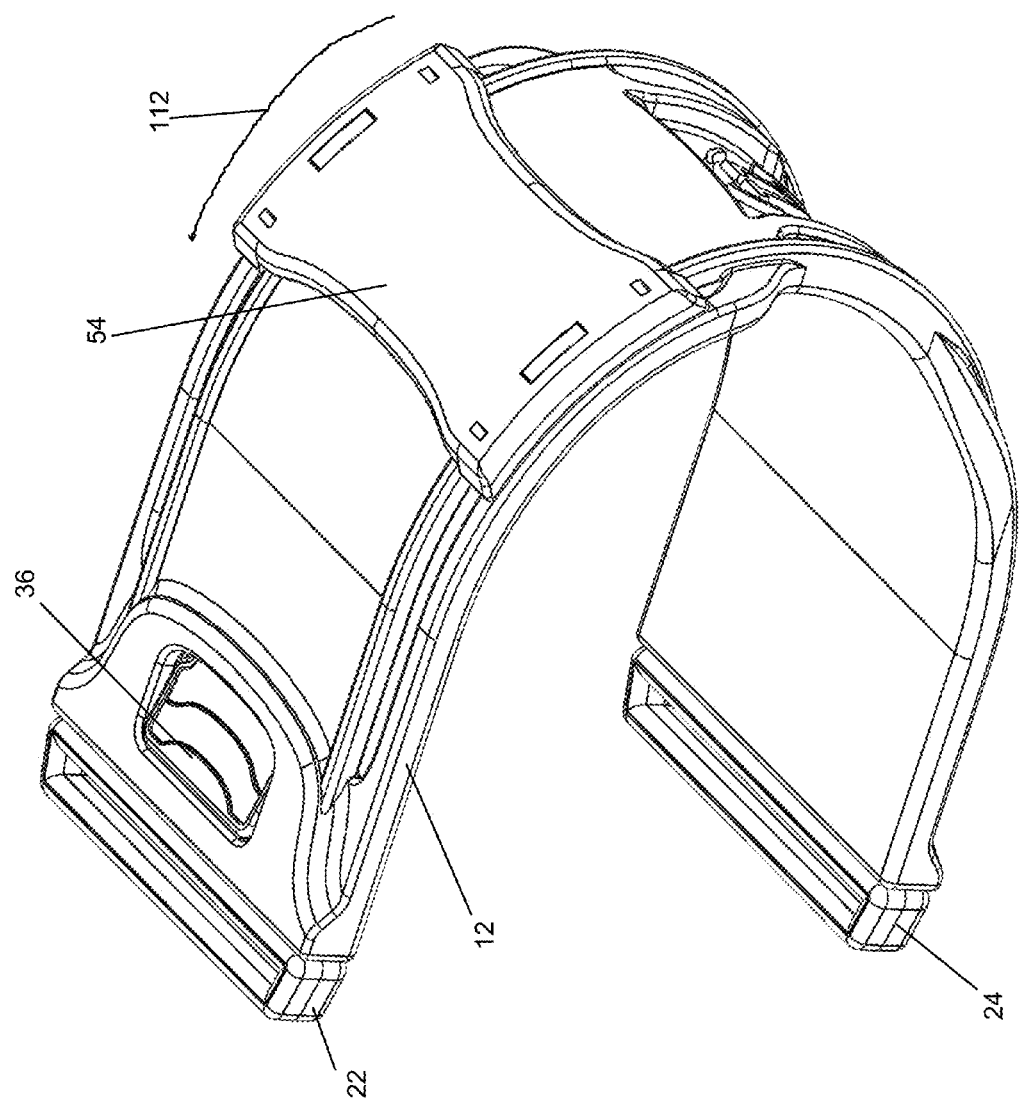
FIGS. 14 and 15 illustrate the radial band brace to demonstrate movement of the bubble assembly along the band brace.
Figure 15:
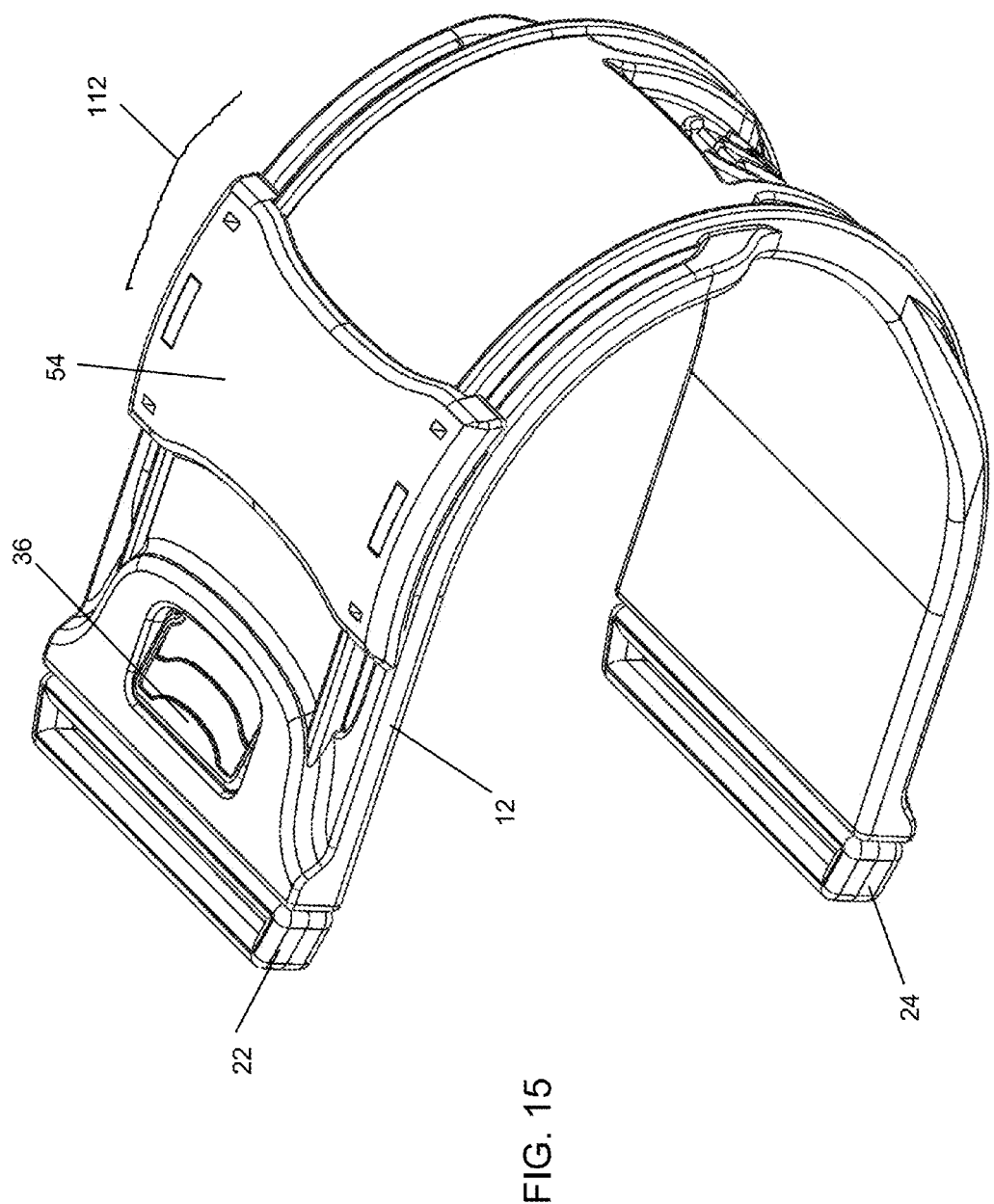

FIGS. 14 and 15 demonstrate movement of the bubble assembly along the band brace, where the bubble assembly has moved up along the brace in the direction of arrow 112.

Figure 16:
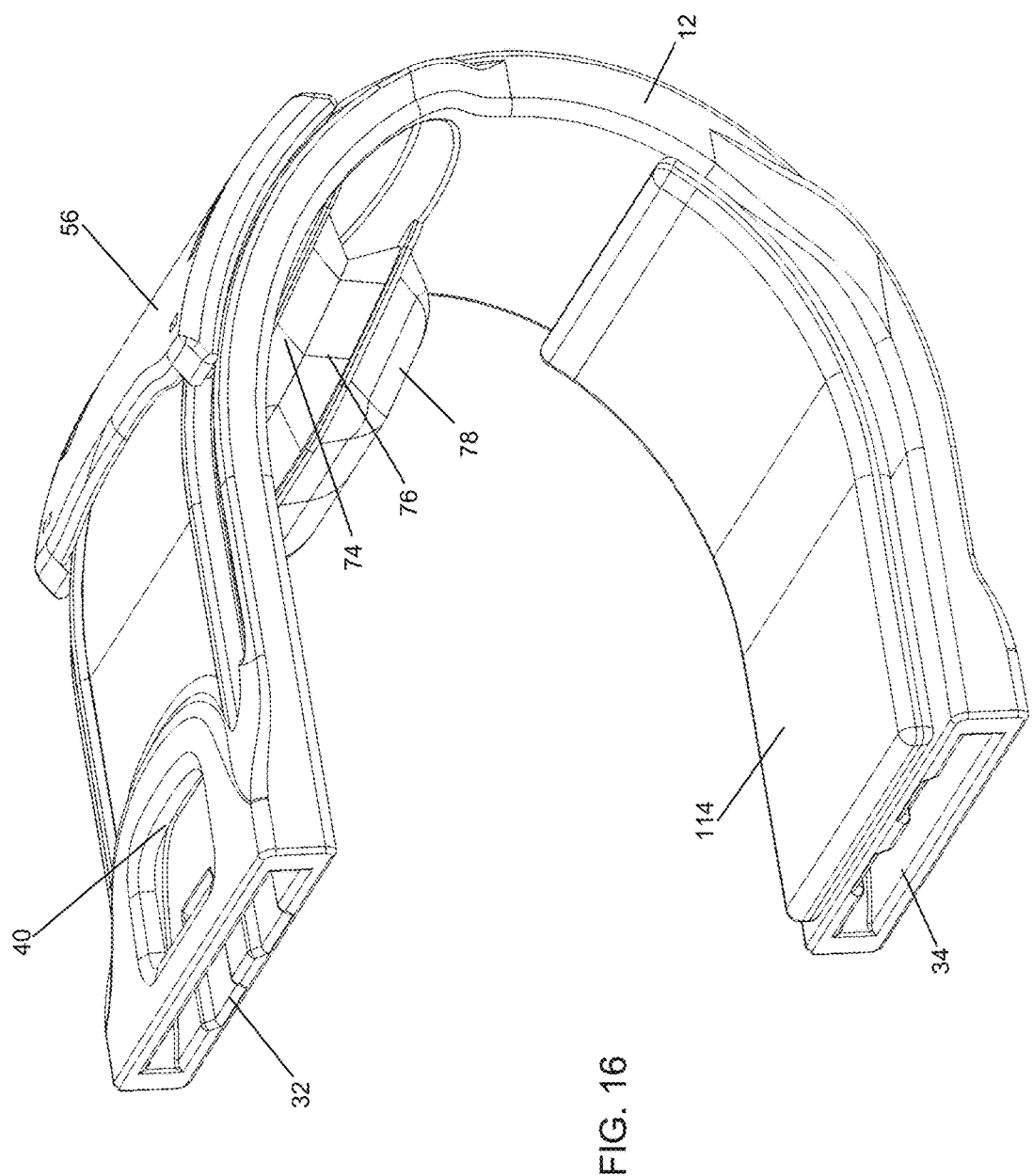
FIG. 16 is a perspective view of the radial band brace with bubble assembly installed, illustrating an optional pad.

FIG. 16 is a perspective view of the radial band brace with bubble assembly installed, illustrating an optional radial band pad 114 (also visible in FIG. 2B) that may be installed at an inner portion of the radial band brace to provide added comfort to the patient and stability to the band. The pad may comprise a foam, for example, or a silicone, or more preferably a low durometer TPE, for example with a 3A shore hardness, which provides a jelly like feel and also provides gripping of the patient's arm, without pulling on hair on the arm. The pad 114 assists in providing pressure in the direction of arrow 160 against the patient's arm.

Figure 17:
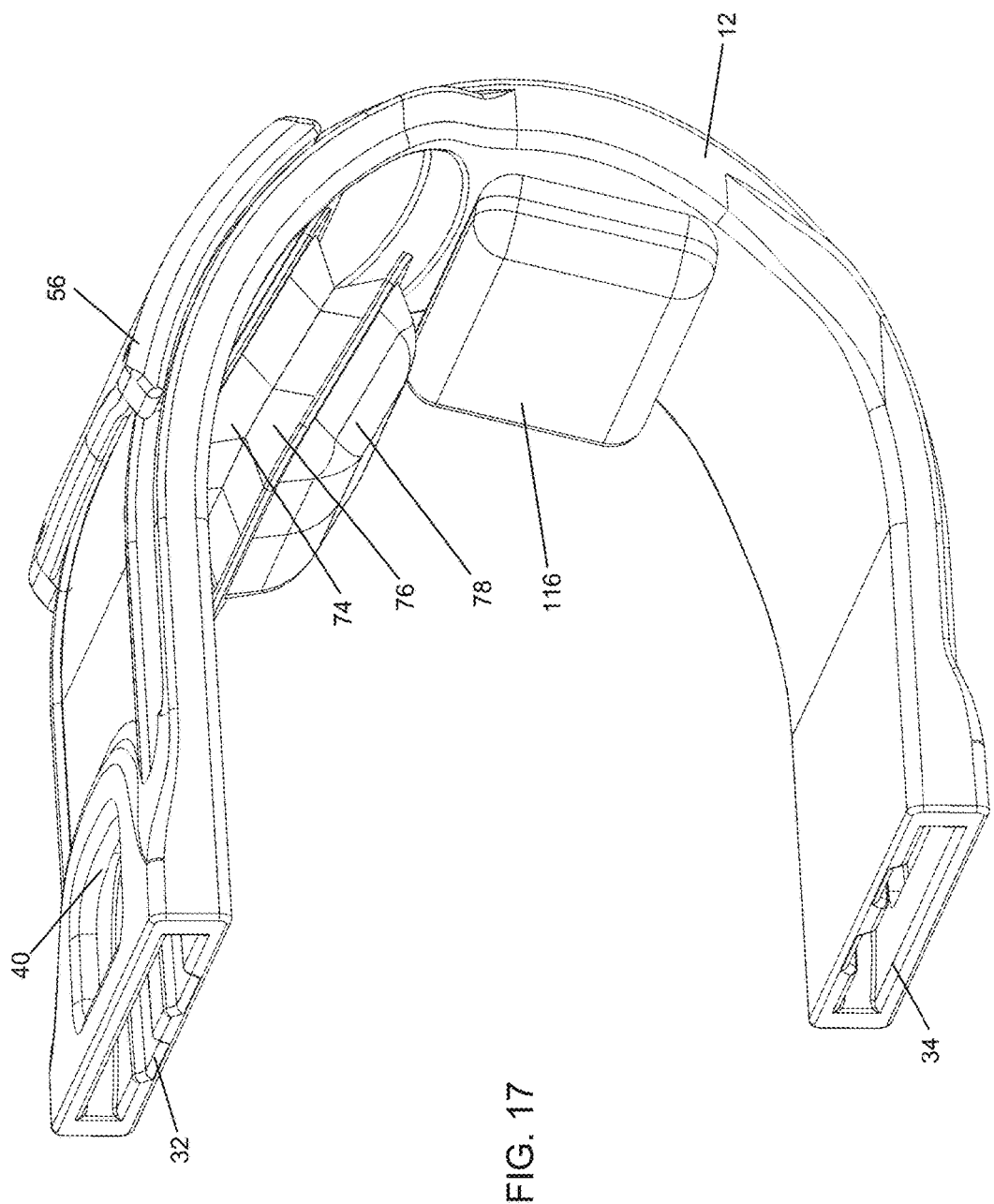
FIG. 17 is a perspective view of the radial band brace with bubble assembly installed, illustrating an optional positioning bubble.

FIG. 17 is a perspective view of the radial band brace with bubble assembly installed, illustrating an optional positioning bubble 116 that may be inflated to assist with positional adjustment on a patient's wrist, which can help in accommodating different wrist sizes and shapes.

Alternative configurations can employ multiple bubbles and a valve or valves to allow selection of which bubbles to inflate, allowing a variety of pressure application choices.

The top bubble brace, bubble layers and the radial band brace (at least in the area the bubble assembly slides over) are suitably made of clear or transparent material to allow unobstructed viewing of the patient's arm through the material. The material can be clear or translucent or even opaque so long as sufficient detail of the site on the patient's arm is visible through the layers to allow accurate positioning. This enables the medical personnel operating the band to precisely position the bubble over the desired spot on the patient's arm to ensure that pressure from the inflated bubble is applied to the proper location. In the configuration illustrated, only 4 layers of material are required to view through, the top bubble brace 68, the radial band brace 12, the top bubble layer 72 and the bottom bubble layer 78. This number could be reduced by, for example, providing a cut out viewing region in the center of the band brace 12 and/or by providing a cut out viewing region in the top bubble brace 68. The top bubble brace may have an indicator line 69 defined therein, to assist with aligning the bubble over the desired pressure point. Alternatively the indicator line may be on the bubble itself, such as on the bottom layer of the bubble. The medical personnel can use the indicator line to position the bubble over the wound site. The indicator line may be of a specific color, such as green, for example. Alternatively, the bottom bubble portion 78 may have such a line 69' (visible in FIG. 19). Since the various layers are clear or translucent, the line is clearly visible from the top surface of the band when it is positioned on the patient. The bubble layers and band in the bubble region can also be provided with a color if desired.

Figure 19:
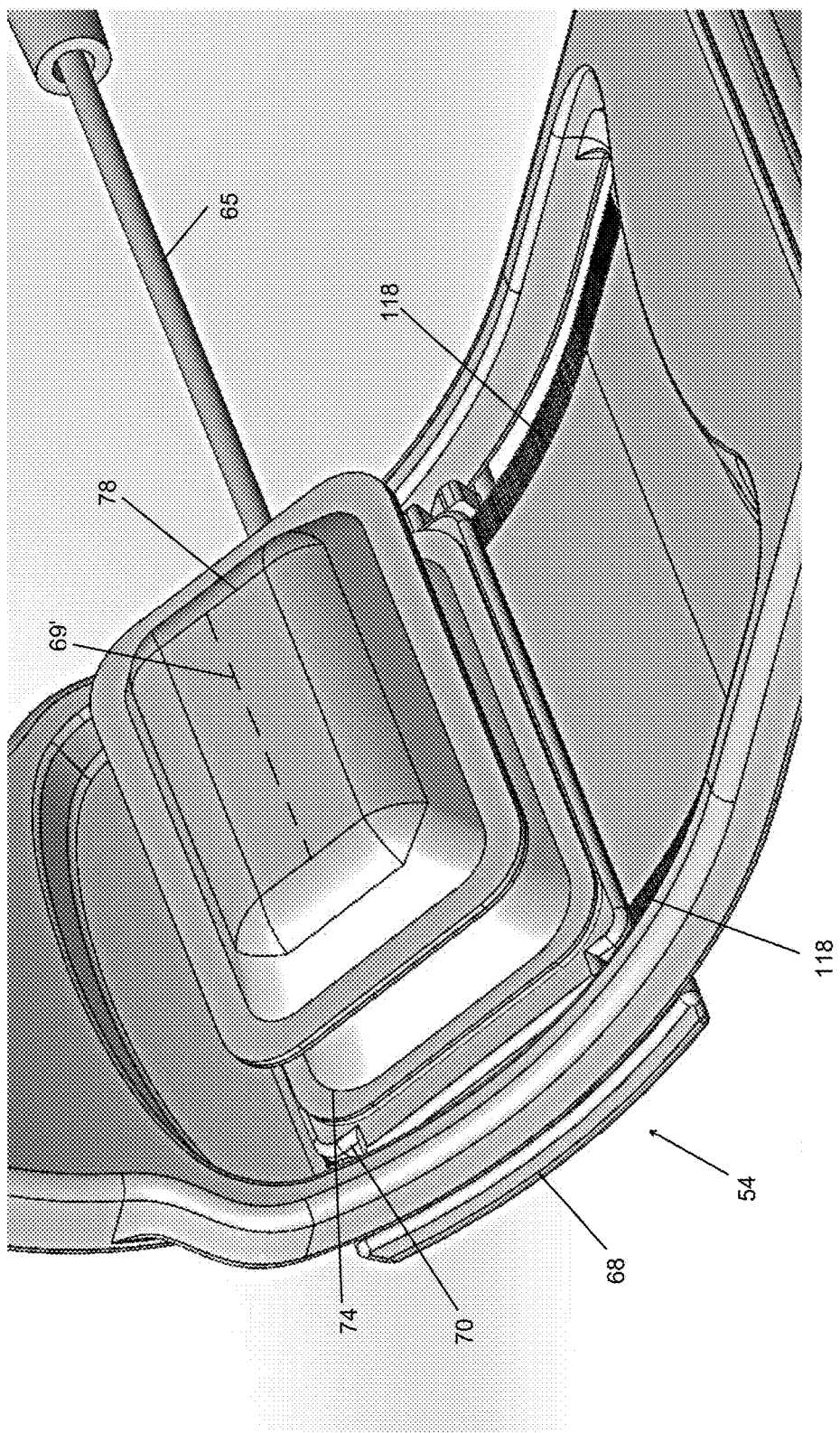
FIG. 19 is a rear partial view illustrating a manner of securing the bubble assembly in position.

FIG. 19 is a rear partial view illustrating a manner of securing the bubble assembly in position. In this configuration, a band of serrations 118 is provided on an inner surface of the band 12 and corresponding projections 120 (indicated in FIG. 6) are provided on counterpart surfaces of bottom bubble brace 70, wherein on inflation of the bubble, the interaction with the bubble and the patient's arm will press the projections 120 into engagement with the serrations 118, to cause the bubble to resist against further sliding, so that the position of the bubble is maintained. An alternative way to secure the bubble without serrations may be understood by reference to FIG. 11, wherein on inflation of the bubble, the upper bubble portion 72 expands such that the upper surface 71 of the bubble portion 72 presses against the inner surface of the central portion 13 of the band 12, and the frictional engagement of the bubble and the band will sufficiently secure the bubble assembly against unintended movement.

Figure 20:
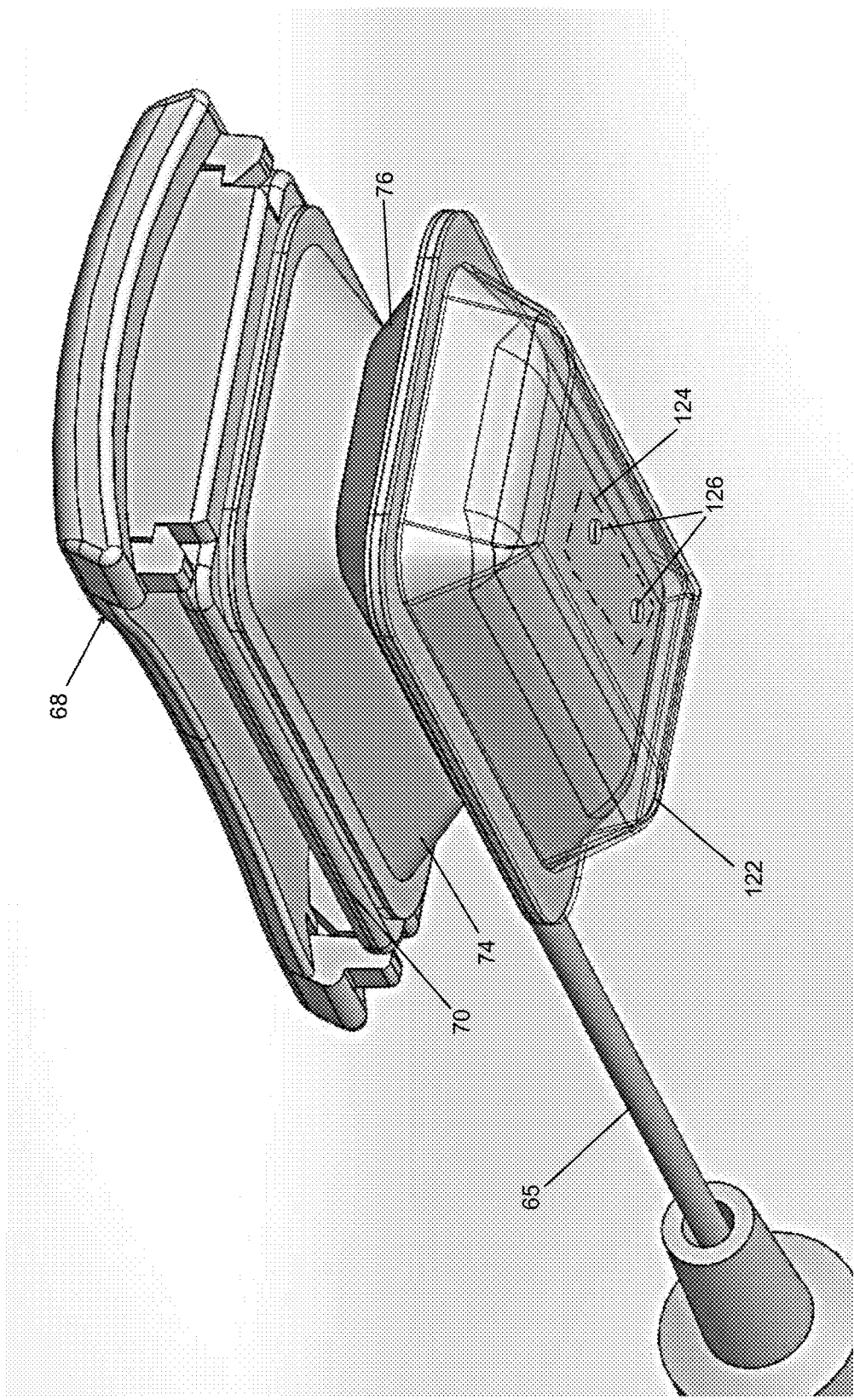
FIG. 20 is a view of an alternative bubble assembly that includes a hemostatic gel or coolant.

In another embodiment, visible in FIG. 20, a view of an alternative bubble assembly that includes a hemostatic gel or coolant, a hemostatic gel 123 may be provided in a receptacle 122 at the bottom bubble layer. A sterile sealing layer 124 may be provided over the gel receptacle, which is then removed just prior to placing the band on the patient, whereby the gel can be dispensed through openings 126 by pressure provided by the inflating bubble exerted on the rear of the receptacle 122.

In still another embodiment, receptacle 122 can contain a cooling element to provide cooling to help retract the artery. The device may then be stored in a refrigerator/freezer prior to use. A combination of cooling element and hemostatic gel may be provided.

Figure 27A:
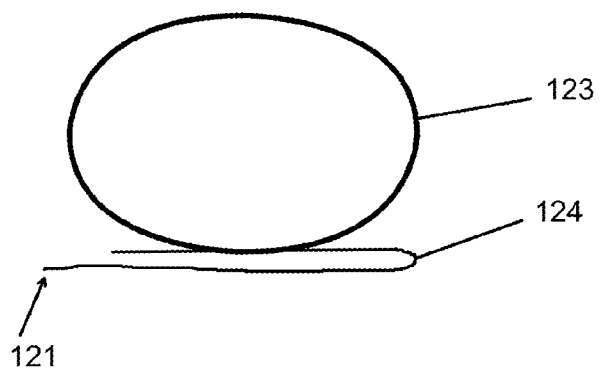
FIGS. 27A-27D illustrate removal of the covering to activate a hemostatic gel or other substance.
Figure 27B:
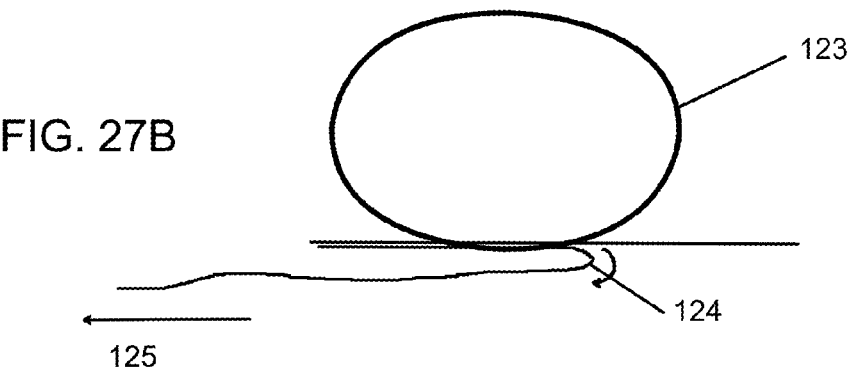
Figure 27C:
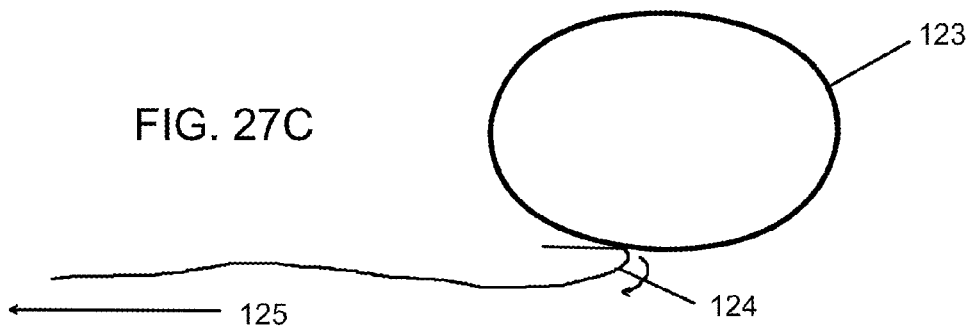
Figure 27D:
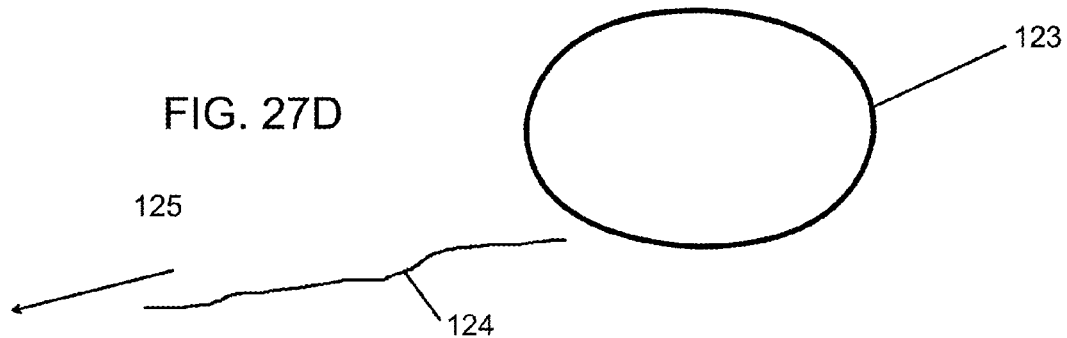

FIG. 27A-D illustrates a manner of removing layer 124, wherein the layer 124 initially covers the gel 123, and comprises a folded over portion, and is pulled from end 121 in the direction of arrow 125 (FIG. 27A). The end of the layer 124 distal from the pulled portion rolls over and begins to peel away from the gel. As the layer is further pulled (FIGS. 27B and 27C), more of the gel is exposed until finally (FIG. 27D), the layer 124 is completely pulled away, exposing the gel fully.

Figure 21:
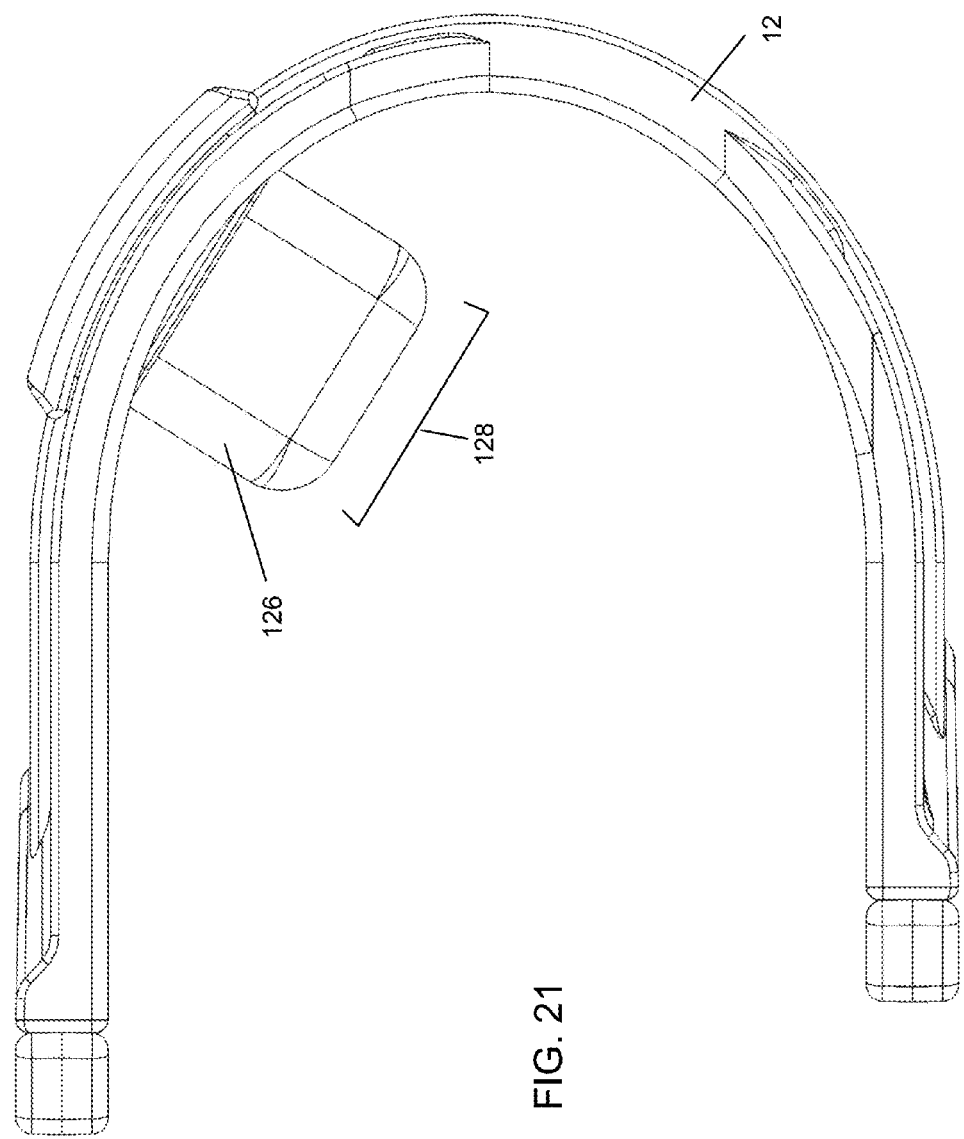
FIGS. 21-25 illustrate exemplary variations of bubble configurations.
Figure 22:
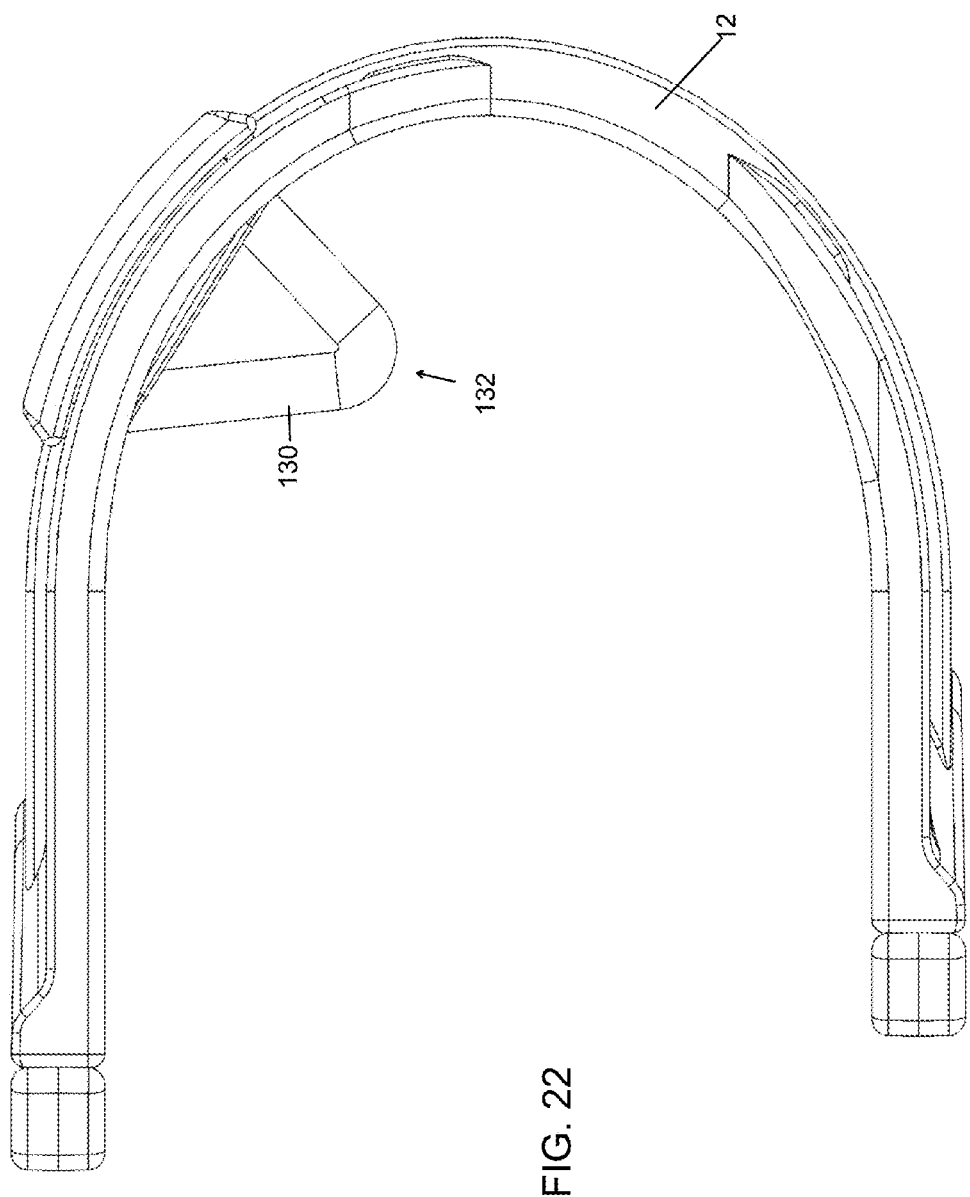
Figure 23:
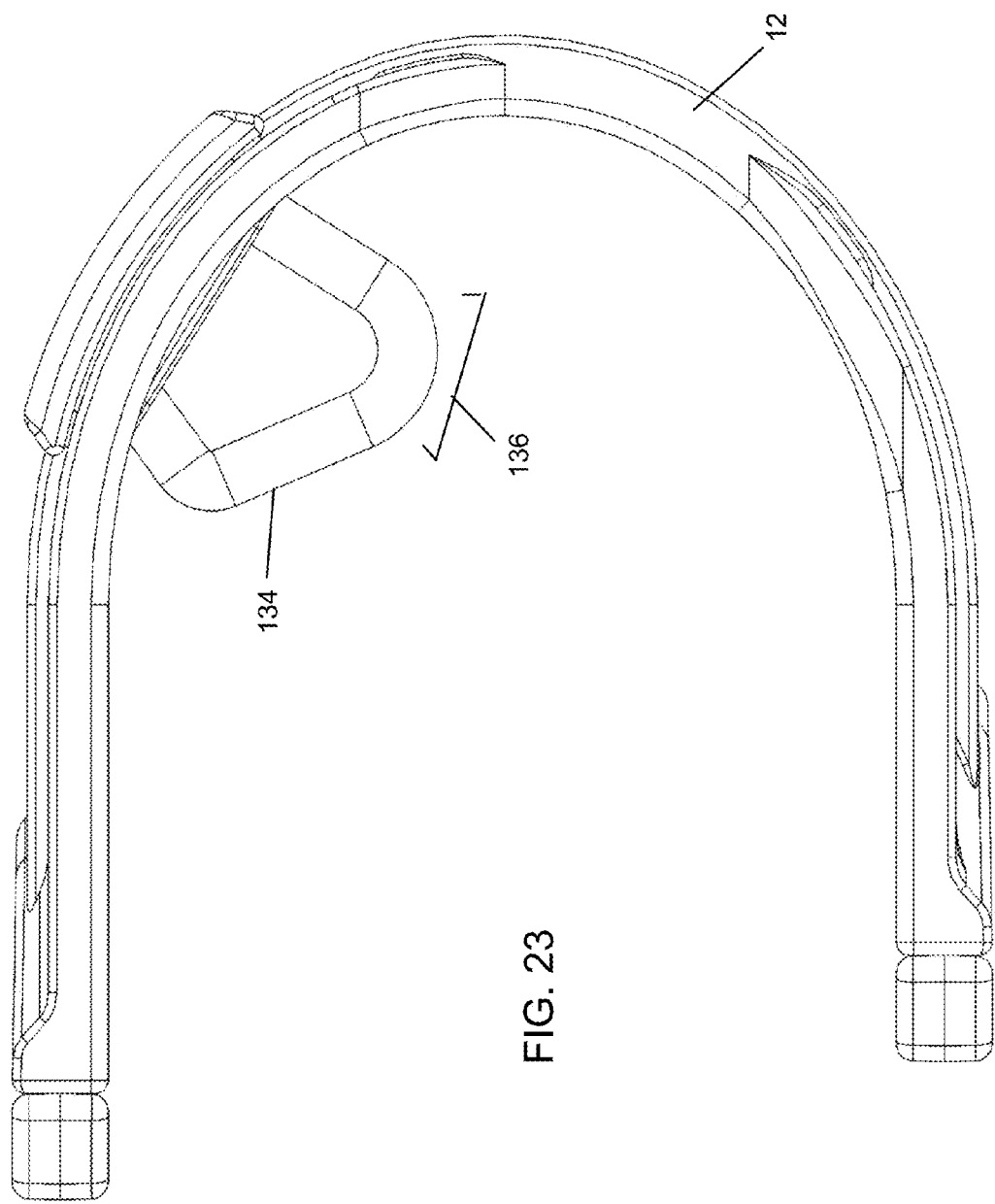
Figure 24:
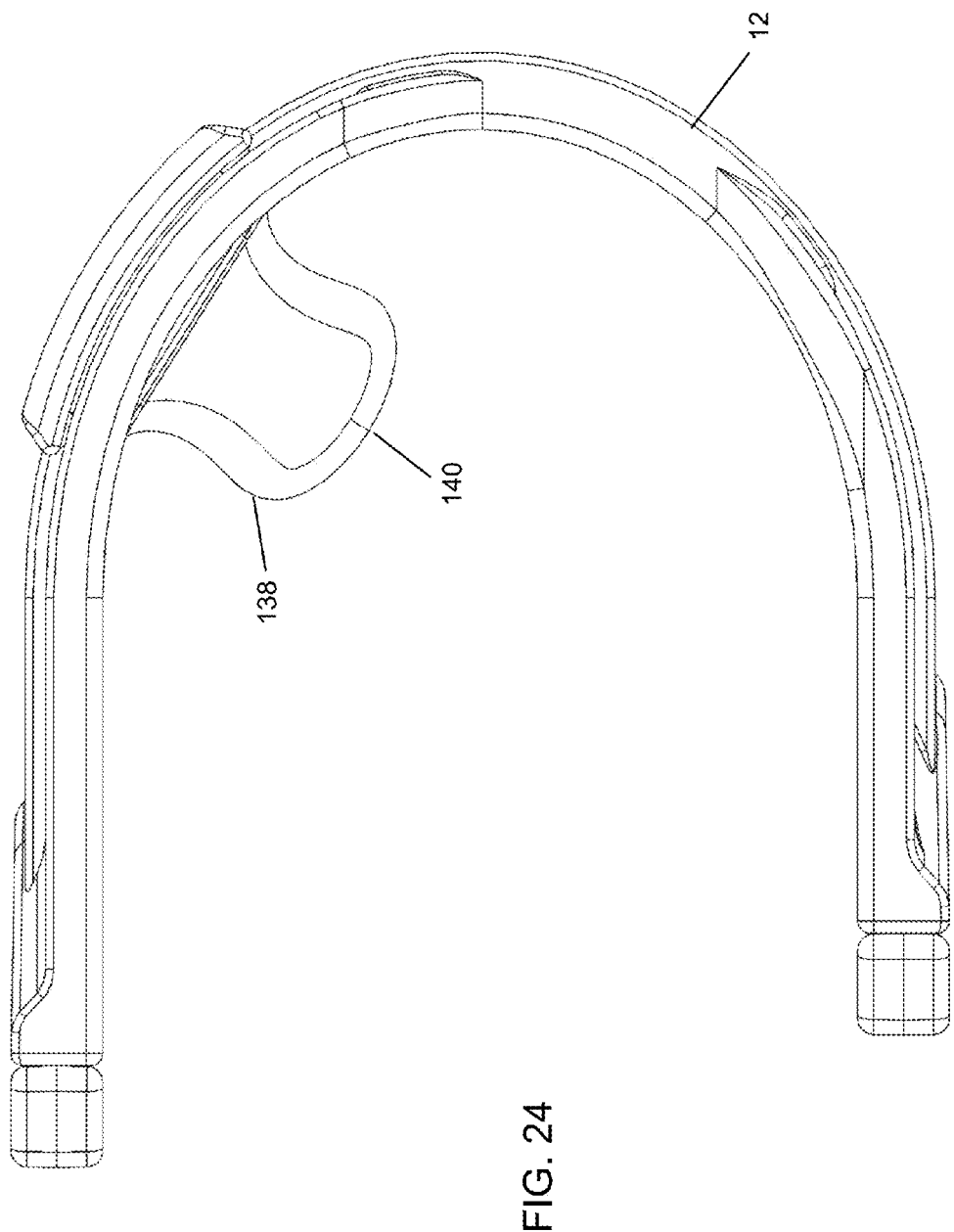
Figure 25:
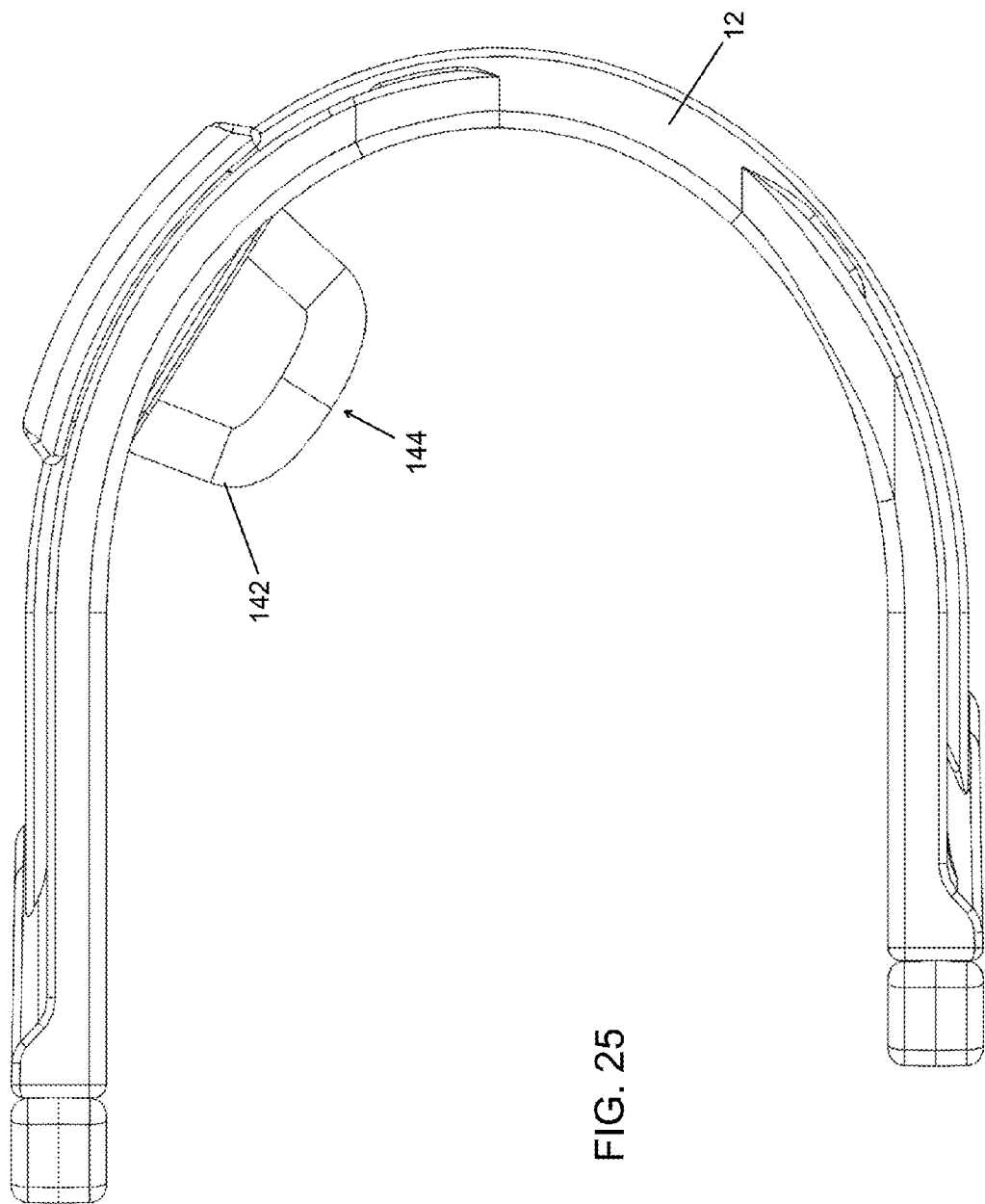

The shape of the bubble portion that directly contact's the patient's arm may be modified for different pressure application profiles. Considering FIGS. 21-25, which are side views of bands without the strap installed, the bubbles can have, for example, a square profile bubble 126 (FIG. 21) for a more flat contact surface 128, a triangular profile bubble 130 providing a narrower contact surface 132 (FIG. 22), a modified square profile 134 with one side longer to provide a wider contact region 136 (FIG. 23), a curved side profile 138 providing a wider more curved contact profile 140 (FIG. 24), and a curved edge rectangular shape 142 providing yet another curved contact surface profile 144. Other shapes may of course be employed to provide desired contact pressure profiles against the patient's arm. The various shapes of the bubbles allow targeted application of pressure to the wrist site along an axis of the bubble, and can be line, oval, rectangular or other shape pressure application profiles, depending on the bubble configuration.

Bubbles having greater length along the direction of the arm's length can be provided for use in applications where a longer incision has been made in the patient, so that pressure is applied over a greater length.

In use of the device, the band portion is slid over the patient's wrist and the strap portions are snapped in place. The bubble is approximately positioned over the insertion site of the catheter, and the strap is tightened. A syringe is attached to the luer lock. The bubble assembly is slid to be in an optimal position, with use of the optional guide mark if desired, and the bubble is inflated, locking the slide against unintended movement. The catheter is removed. If bleeding starts immediately, the bubble is inflated further. If no bleeding is observed, pressure is released until just the point that bleeding starts, whereupon 2 cc of air (or other fluid) are added, the syringe is removed from the luer lock, and after 30-60 minutes, as determined by the medical personnel, then 2 cc are removed from the bubble every 5 minutes. Once it is determined that hemostatic has been achieved, the bubble is deflated and slid away from the site. The sideward movement of the bubble reduces the chance of tearing the clotted seal on the artery away as opposed to pulling directly upwardly as with prior art solutions.

The disclosed band has numerous benefits over prior solutions. The attachment of the band to the arm is separate from final positioning of the bubble over the site. The slidable bubble assembly allows precise positioning of the bubble for maximum effect. The bubble is typically smaller than prior art devices, and can provide a pinpoint focus of pressure. The pressure applied by the inflated bubble pushes off axis, as indicated by arrow 158 in FIG. 2A, pushing the artery directly into the patient's bone, not merely pushing the artery in a direction that might not be normal to the bone, which would be less effective. The angle at which the pressure is applied can be varied in accordance with the disclosure. The number of surfaces through which the site is viewed is reduced over prior solutions. When deflated, the bubble retracts into itself and forms a concavity relative to the skin to keep the bubble away from contact with the skin. Unlike prior devices, the band and bubble location will not substantially rotate when the bubble is inflated. The device is easily put onto a patient's wrist by sliding the band onto the wrist from the side, then the strap may be clipped in and tightened to secure the band on the patient. The patient's wrist need not be lifted to install the band. While traditional devices tend to constrict the patient's entire wrist, almost acting like a tourniquet, the relatively rigid material of the band of the present device instead acts as a hinge, keeping pressure from being applied to the entire wrist, allowing specific pressure application where needed by the bubble, which mimics pressure applied by a finger by medical personnel, as is done when no radial band is available. The bubble in the illustrated configurations is suitably inflatable to 10 psi, which is more than sufficient. While the illustrated inflation medium is air, fluid or other gases may be employed to inflate the bubble. The bubble can be provided with a slow rate leak, such that it will slowly deflated over time on its own without intervention, so that after a sufficient time to allow hemostasis, the bubble pressure is released. The skin contact surface of the bubble can be provided with a medication or other substance to assist with the function.

The illustrated application of the device is with radial artery procedures, but other uses are possible, such as with stopping bleeding in dialysis procedures, for example.

While a preferred embodiment of the technology has been shown and described, it will be apparent to those skilled in the art that many changes and modifications may be made without departing from the broader aspects. The appended claims are therefore intended to cover all such changes and modifications as fall within the true spirit and scope of the technology.

What is claimed is:

1. A hemostasis device, comprising:
   an attachment device for securing the hemostasis device to a patient, said attachment device comprising a substantially rigid substantially U-shaped partial cuff member adapted to fit over a patient's body;

a positionable inflatable pressure application device for positioning over a site on the patient's body independent of securing of the attachment device; and a radial comfort and stability pad positioned at a surface of the U-shaped cuff member that is to be positioned adjacent the patient's body, said radial comfort and stability pad positioned at a side of the cuff that contacts a part of the patient's body opposite the side of the part of the patient's body at which pressure is applied by the inflatable pressure application device.

2. The hemostasis device according to claim 1, wherein said attachment device further comprises a strap member removably attachable between an end of a first side leg of the U-shaped partial cuff member and an end of a second side leg of the U-shaped partial cuff member, for enabling the hemostasis device to be secured to the patient's body.

3. The hemostasis device according to claim 2 wherein said strap member comprises at least one buckle to removably attach to at least one of said first and second side legs of said U-shaped partial cuff member.

4. The hemostasis device according to claim 3 wherein said at least one buckle and said cuff member comprise a tab portion and a corresponding slot portion adapted to receive said tab portion in releasably locking engagement.

5. The hemostasis device according to claim 1, wherein said positionable inflatable pressure application device comprises an inflatable member adapted to press against the patient when inflated.

6. The hemostasis device according to claim 5 wherein said inflatable member includes a substantially clear viewing portion for enabling viewing through said inflatable member of the position on the patient where said inflatable member presses when inflated.

7. The hemostasis device according to claim 5 wherein said inflatable member collapses to retract away from the patient when deflated.

8. The hemostasis device according to claim 1 wherein said positionable inflatable pressure application device slides along a portion of the attachment device for positioning thereof.

9. The hemostasis device according to claim 1, said inflatable pressure application device further comprising a receptacle for holding a substance wherein the substance is dispensed to the patient by pressure provided by the pressure application device.

10. The hemostasis device according to claim 9, wherein said substance comprises a hemostatic substance.

11. The hemostasis device according to claim 9, wherein said receptacle comprises a removable sterile sealing layer.

12. A hemostasis band device for attaching to a patient's body to provide pressure against a puncture site on the patient's body while awaiting hemostasis comprising:
an attachment band for engaging the patient's body, said attachment band comprising a substantially rigid substantially U-shaped partial cuff member adapted to fit over the patient's body;
a positionable inflatable pressure application member for positioning over the puncture site on the patient's body independent of engaging of the attachment band, said positionable inflatable pressure application member moving position along a portion of the attachment band for positioning of the pressure application member relative to the patient's body without requiring repositioning of the attachment band; and
a securement strap that attaches to first and second ends of the U-shaped partial cuff to secure the cuff member to the patient's body, said securement strap being removably attachable to at least one of said first and second ends,
further comprising a radial comfort and stability pad positioned at a surface of the cuff that is adjacent the patient's body, said radial comfort and stability pad positioned at a side of the cuff that contacts a part of the patient's body opposite the side of the part of the patient's body at which pressure is applied by the inflatable member.

13. The hemostasis band device according to claim 12, further comprising a locking device for substantially locking said positionable inflatable pressure application member in location relative to the substantially rigid substantially U-shaped partial cuff member when positioned over the puncture site.

14. The hemostasis band device according to claim 12, wherein said inflatable pressure application member includes a substantially clear viewing portion for enabling viewing through said inflatable pressure member of the puncture site on the patient where said inflatable member presses when inflated.

15. A hemostasis wrist band comprising:
a wrist engaging portion adapted for placement on a patient's wrist; and
a positionable pressure bubble member adapted to slide along a portion of the wrist engaging portion for positioning of the pressure bubble member over a desired pressure application location, further comprising:
a radial comfort and stability pad positioned at a surface of the wrist engaging portion that is to be positioned adjacent the patient's wrist, said radial comfort and stability pad positioned at a side of the wrist engaging portion that contacts a part of the patient's wrist opposite the side of the part of the patient's wrist at which pressure is applied by the positionable pressure bubble member.

16. The hemostasis wrist band according to claim 15, wherein said pressure bubble member has a viewing portion that is substantially clear to enable viewing of a pressure application site through the pressure bubble member.

17. The hemostasis wrist band according to claim 15, wherein said wrist engaging portion is substantially rigid.

18. The hemostasis wrist band according to claim 15 further comprising a locking device for substantially locking said positionable pressure bubble member in location relative to the wrist engaging portion when positioned to a desired location.

19. The hemostasis wrist band according to claim 15, further comprising an inflation member for allowing inflation/deflation of the pressure bubble member.

20. The hemostasis wrist band according to claim 19 wherein said inflation member comprises a leur lock attachment for connection to a pressure source.

21. The hemostasis wrist band according to claim 15, wherein said pressure bubble member further comprises a receptacle for holding a substance wherein the substance is dispensed to the patient by pressure provided by the pressure bubble member.

22. The hemostasis wrist band according to claim 21, wherein said substance comprises a hemostatic substance.

23. The hemostasis wrist band according to claim 21, wherein said receptacle comprises a removable sterile sealing layer for sealing the receptacle against contamination until use.

* * * * *